US009835630B2

(12) United States Patent
Keshavjee et al.

(10) Patent No.: US 9,835,630 B2
(45) Date of Patent: Dec. 5, 2017

(54) METHODS AND COMPOSITIONS FOR ASSESSING LUNG GRAFTS

(71) Applicant: University Health Network, Toronto (CA)

(72) Inventors: Shaf Keshavjee, Toronto (CA); Marcelo Cypel, Toronto (CA); Mingyao Liu, North York (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/768,948

(22) PCT Filed: Feb. 20, 2014

(86) PCT No.: PCT/CA2014/000138
§ 371 (c)(1),
(2) Date: Aug. 19, 2015

(87) PCT Pub. No.: WO2014/127462
PCT Pub. Date: Aug. 28, 2014

(65) Prior Publication Data

US 2015/0377904 A1 Dec. 31, 2015

Related U.S. Application Data

(60) Provisional application No. 61/766,862, filed on Feb. 20, 2013.

(51) Int. Cl.
*G01N 33/00* (2006.01)
*G01N 33/68* (2006.01)
*C40B 30/02* (2006.01)

(52) U.S. Cl.
CPC ......... *G01N 33/6884* (2013.01); *C40B 30/02* (2013.01); *G01N 33/68* (2013.01);
(Continued)

(58) Field of Classification Search
CPC ..... G01N 33/6884; G01N 33/68; C40B 30/02
See application file for complete search history.

(56) References Cited

U.S. PATENT DOCUMENTS

2012/0330438 A1* 12/2012 Keshavjee ........... A01N 1/0215 623/23.65

OTHER PUBLICATIONS

Sadaria et al., (Annals of Thoracic Surgery. 2011;92:478-484).*
(Continued)

*Primary Examiner* — Cherie M Stanfield
(74) *Attorney, Agent, or Firm* — Bereskin & Parr LLP; Carmela De Luca

(57) ABSTRACT

A method of classifying a lung graft subjected to normothermic ex vivo lung perfusion (EVLP), during perfusion and/or after perfusion, the method comprising: a) collecting a test sample from the lung graft; b) measuring a polypeptide level of a negative transplant predictor gene product selected from CCG predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1 in the sample and/or determining a metabolite profile of the sample for lung grafts that are from donors where the death was due to cardiac death (DCD); c) identifying the graft as a good candidate for transplant or a poor candidate for transplant wherein an increased polypeptide level of one or more negative transplant outcome predictor gene products compared to an outcome control or a reference metabolic profile is indicative the graft is a poor candidate for transplant.

13 Claims, 26 Drawing Sheets

Study Design

Help Trial from Sep 2009 to Nov 2012

80 EVLPs 45 bilateral transplants*
15 unilateral transplants
4 bilobar transplants 27 good outcome
7 PGD3
3 bridged ECLS
16 declined EVLP perfusate samples were collected at 1 hour and 4 hours of perfusion
* 8 early cases without perfusates available

(52) U.S. Cl.
CPC ................ *G01N 2333/5754* (2013.01); *G01N 2800/245* (2013.01)

(56) References Cited

OTHER PUBLICATIONS

Salama et al., (Am J Transplant. 2010.10:628-636).*
Cypel et al., (N Engl J Med. Apr. 14, 2011; 364(15):1431-40).*
Marcelo Cypel et al. "T Normothermic Ex Vivo Lung Perfusion in Clinical Lung Transplantation From the Toronto Lung Transplant Program (Abstract) Background" N Engl J Med. Jan. 2011, pp. 1431-1440.
M. Salama et al. "Concomitant Endothelin-1 Overexpression in Lung Transplant Donors and Recipients Predicts Primary Graft Dysfunction", American Journal of Transplantation, vol. 10, No. 3, Mar. 1, 2010, pp. 628-636.
Mohamed Salama et al. "Endothelin-1 is a useful biomarker for early detection of bronchiolitis obliterans in lung transplant recipients", Journal of Thoracic and Cardiovascular Surgery, vol. 140, No. 6, Dec. 1, 2010, pp. 1422-1427.
T. Okamoto et al. "Ex Vivo Lung Perfusion of Rejected Human Donor Lungs; Are Donor Lungs with Prolonged Cold Ischemic Time Re-Conditioned by EVLP?" Journal of Heart and Lung Transplantation, vol. 32, No. 4, Apr. 1, 2013, pp. S67.
Machuca Tiago Noguchi et al., "The Role of the Endothelin-1 Pathway as a Biomarker for Donor Lung Assessment in Clinical Ex Vivo Lung Perfusion" Journal of Heart and Lung Transplantation, vol. 34, No. 6, Jun. 2015, pp. 849-857.
Sadaria et al. Cytokine Expression Profile in Human Lungs Undergoing Normothermic Ex-Vivo Lung Perfusion. Annals of Thoracic Surgery, 2011, vol. 92, pp. 478-484.
Kaneda et al. Pre-Implantation Multiple Cytokine mRNA Expression Analysis of Donor Lung Grafts Prdicts Survival After Lung Transplantation in Humans. American Journal of Transplantation, 2006, vol. 6, issue 3, pp. 544-551.
Saito et al. Impact of Cytokine Expression in the Pre-Implanted Donor Lung on the Development of Chronic Lung Allograf Dysfunction Subtypes. American Journal of Transplantation, 2013, vol. 13, issue 12, pp. 3192-3201.

* cited by examiner

EVLP perfusate samples were collected at 1 hour and 4 hours of perfusion

* 8 early cases without perfusates available

4 hour analytes higher in PGD3 group

Study groups: perfusate samples at 1 hour and 4 hours EVLP
Analysis by ELISA for ET-1, Big ET-1 and ET-1 Converting Enzyme

At 1 hour of EVLP, levels of ET-1 and Big ET-1 are significantly higher in declined lungs A) Endothelin-1 at 1 hour of EVLP B) Big Endothelin-1 at 1 hour of EVLP

At 4 hours of EVLP, levels of ET-1 and Big ET-1 are significantly higher in declined lungs A) Endothelin-1 at 4 hours of EVLP B) Big Endothelin-1 at 4 hours of EVLP At 4 hours of EVLP, levels of ET-1 and Big ET-1 are significantly higher in both PGD3 and declined lungs High accuracy of ET-1 at 4 hours of EVLP to diagnose both Declined and PGD3 cases from donors after cardiac death Fig. 9
High accuracy of Big ET-1 at 4 hours of EVLP to diagnose both Declined and PGD3 cases from donors after cardiac death
A) ROC curve Control vs Declined for Big ET-1 at 4 hours of EVLP
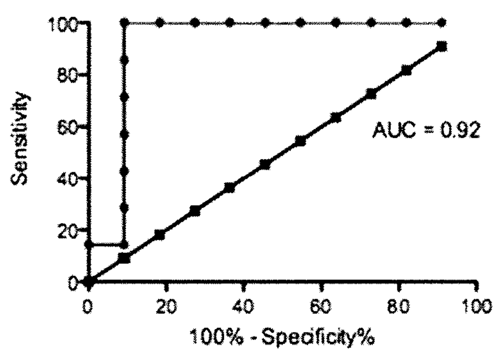
B) ROC curve Control vs PGD3 for Big ET-1 at 4 hours of EVLP
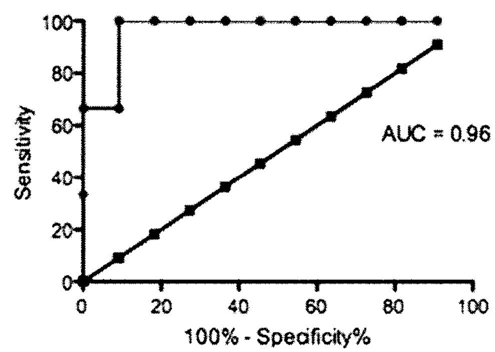

A)

Fig. 10 (continued)
B)
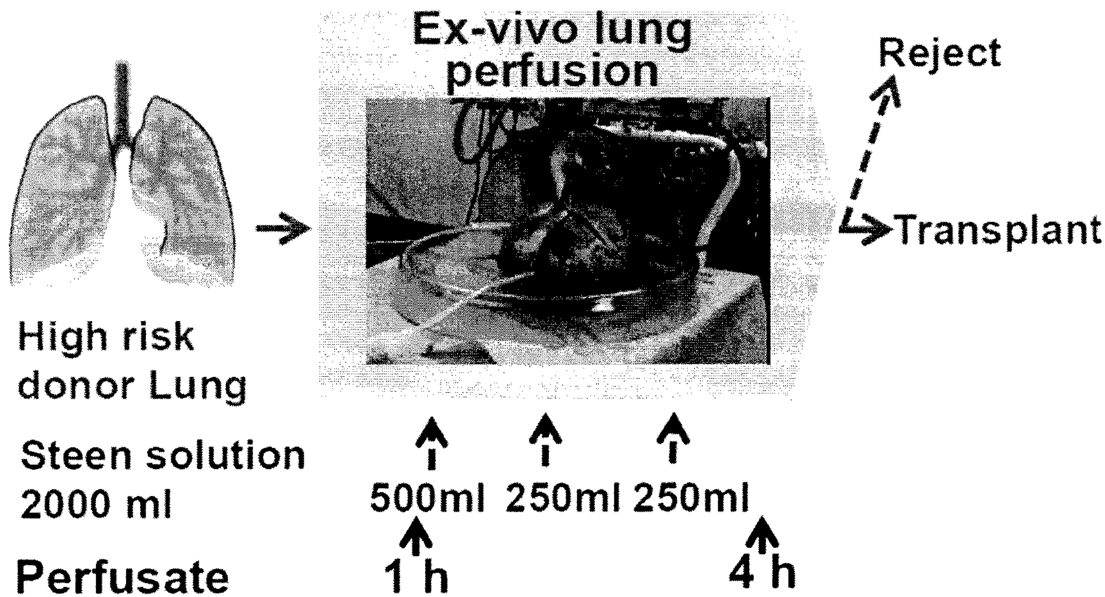
C)
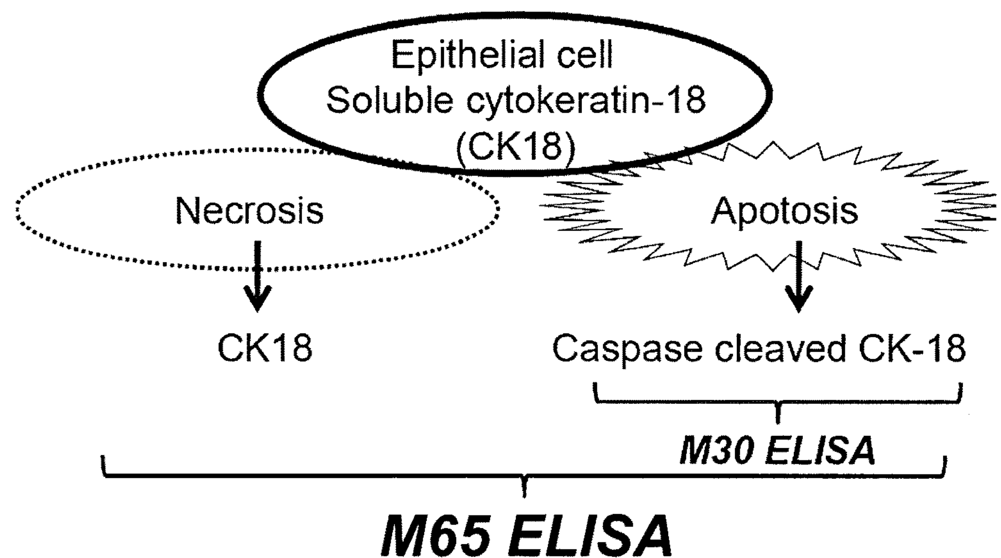

D)

Fig. 11
A)
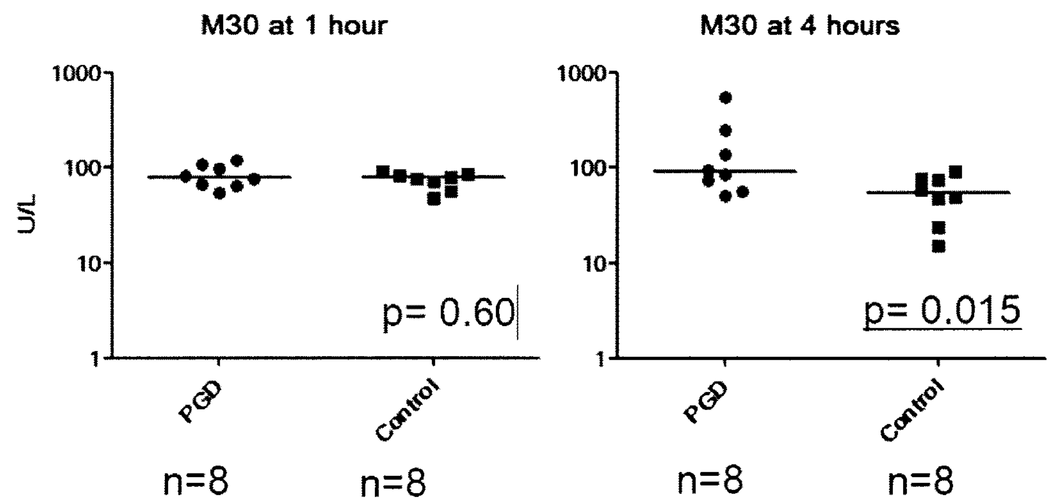
Mann-Whitney's test. Data is shown in logarithmic display
B)
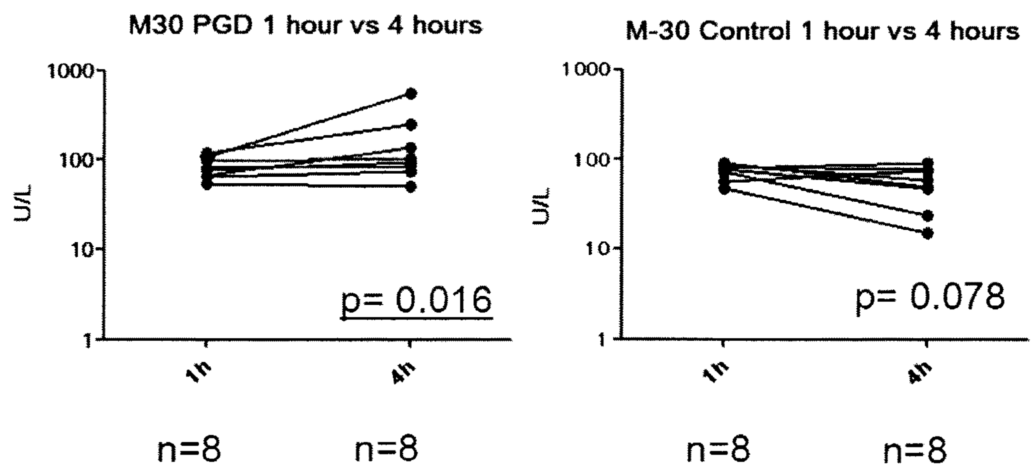
Wilcoxon signed-rank test.
Data is shown in logarithmic display

C)

Mann-Whitney's test. Data is shown in logarithmic display

Fig. 12
A)
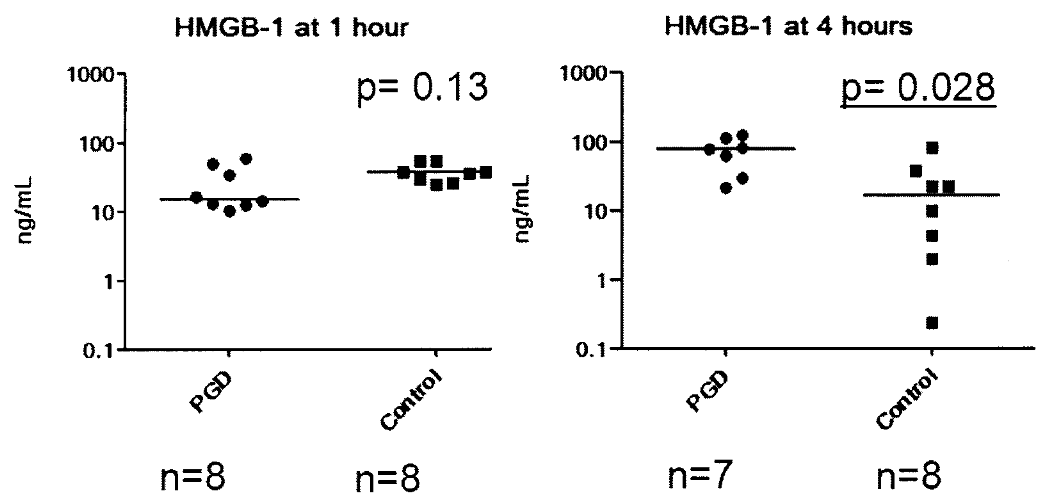
Mann-Whitney's test. Data is shown in logarithmic display
B)
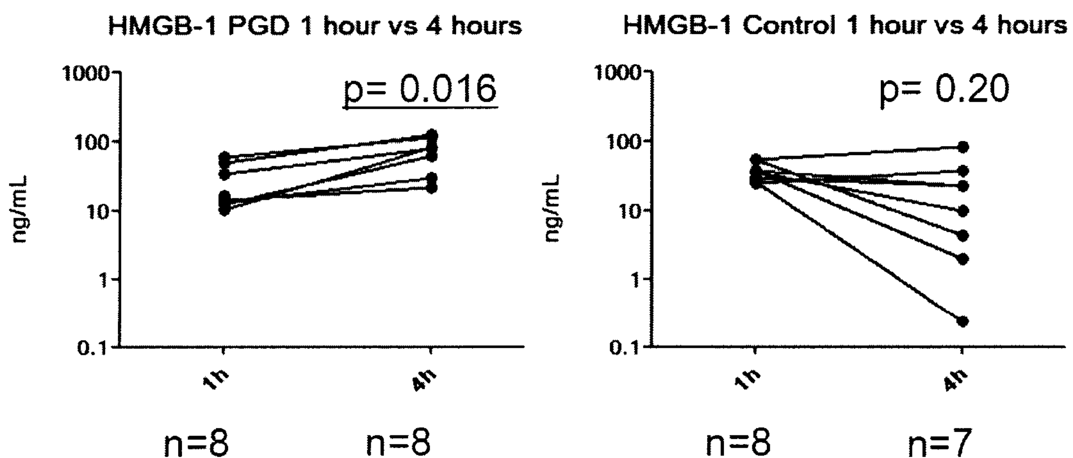
Wilcoxon signed-rank test.
Data is shown in logarithmic display Fig. 13
A)
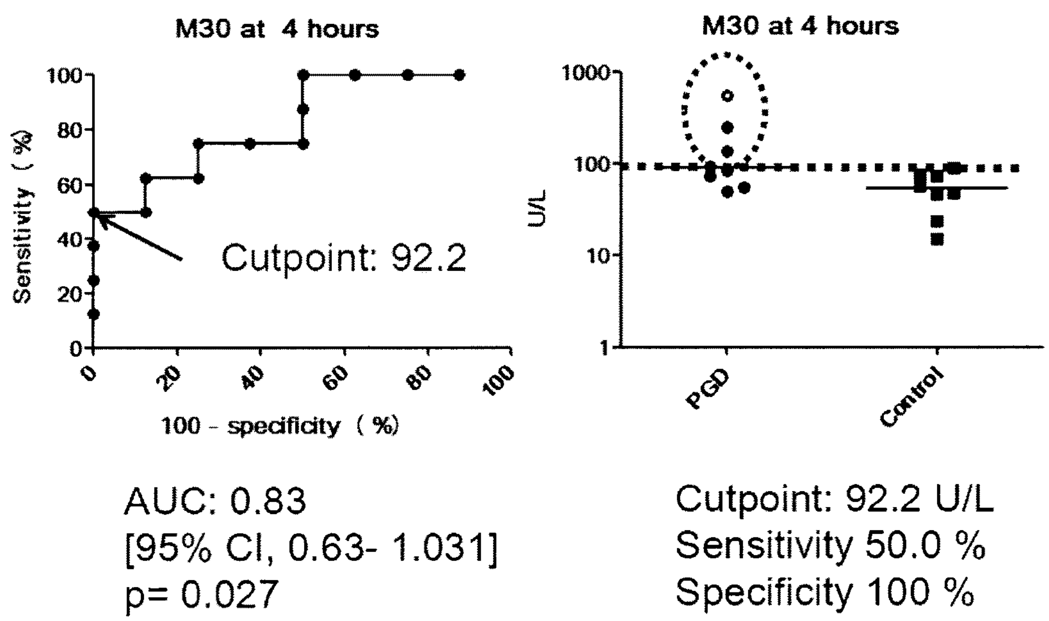
B)
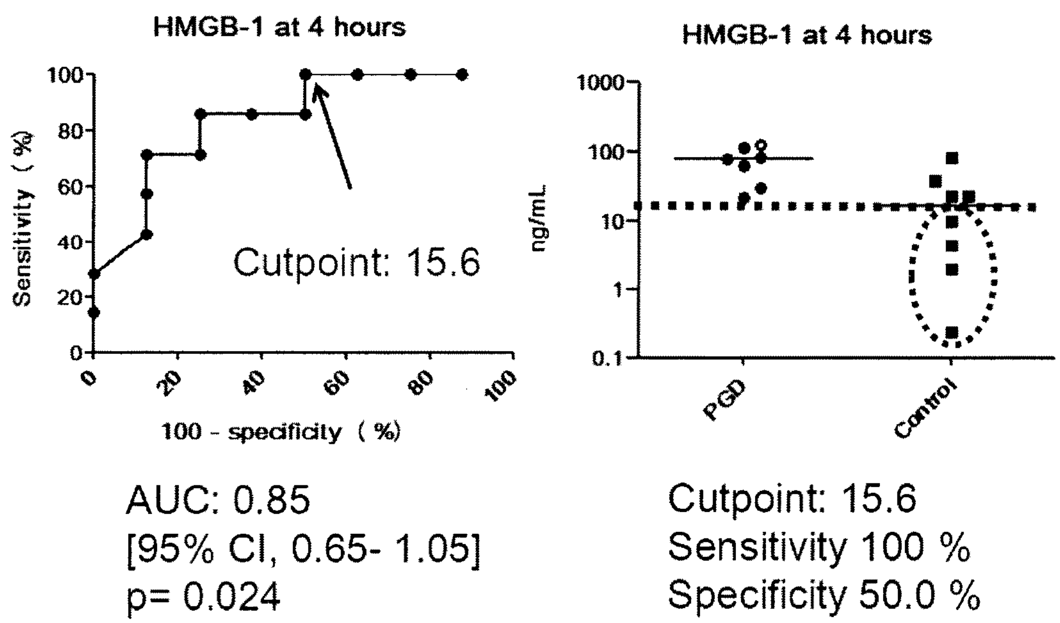

Fig. 14

Start EVLP DCD: Bad vs Good; Adjusted p Value < 0.10 (n=10)

| ID | P.Value | adj.P.Val | FoldChange |
|---|---|---|---|
| 5-aminovalerate | 1.11E-05 | 0.00335271 | 3.429835338 |
| taurocholate | 5.56E-05 | 0.00562692 | 6.14621888 |
| glycocholate | 5.59E-05 | 0.00562692 | 4.467234694 |
| betaine | 0.0004735 | 0.03574886 | 1.839589363 |
| histidine | 0.0007537 | 0.04552173 | 3.188382657 |
| deoxycarnitine | 0.0010416 | 0.05242607 | 1.597118982 |
| pyridoxate | 0.0014819 | 0.06393472 | 1.798123743 |
| urea | 0.0019215 | 0.07253831 | 44.81071356 |
| propionylcarnitine | 0.0024487 | 0.082166 | 1.476916266 |
| pyroglutamine | 0.0030876 | 0.0932442 | 2.40154283 |

Fig. 15

End EVLP DCD Bad vs Good; Adjusted p Value < 0.05 (n=40)

| ID | P.Value | adj.P.Val | FoldChange |
|---|---|---|---|
| betaine | 1.06E-05 | 0.00320844 | 2.188894717 |
| N-acetylneuraminate | 4.10E-05 | 0.00618932 | 8.236247476 |
| malate | 9.38E-05 | 0.00944375 | 2.728521966 |
| glycocholate | 0.0001507 | 0.01137838 | 4.05727746 |
| alpha-hydroxyisocaproate | 0.0002157 | 0.01170798 | 3.033114583 |
| 3-methyl-2-oxobutyrate | 0.0002326 | 0.01170798 | 1.739706084 |
| taurocholate | 0.0002969 | 0.01280875 | 5.031679989 |
| 2-methylbutyroylcarnitine | 0.0003814 | 0.01341463 | 1.957533168 |
| pipecolate | 0.0004031 | 0.01341463 | 2.267620925 |
| 4-methyl-2-oxopentanoate | 0.0004442 | 0.01341463 | 1.689847624 |
| methionine | 0.0011141 | 0.02529794 | 1.626766106 |
| phenylalanine | 0.0011271 | 0.02529794 | 1.534495168 |
| 5,6-dihydrouracil | 0.0011509 | 0.02529794 | 2.723018601 |
| pro-hydroxy-pro | 0.0011728 | 0.02529794 | 1.699192817 |
| histidine | 0.001401 | 0.02820769 | 2.991863684 |
| trans-4-hydroxyproline | 0.0015952 | 0.02993462 | 4.546712972 |
| N1-methylguanosine | 0.0016851 | 0.02993462 | 1.702527118 |
| valine | 0.0019774 | 0.03160743 | 1.440733422 |
| trans-urocanate | 0.0019885 | 0.03160743 | 2.068592646 |
| 2-aminobutyrate | 0.0021129 | 0.03190525 | 2.89833243 |
| phosphate | 0.0025117 | 0.03474228 | 1.438769915 |
| lactate | 0.0025367 | 0.03474228 | 1.425701341 |
| leucine | 0.0026932 | 0.03474228 | 1.489851333 |
| isoleucine | 0.0027966 | 0.03474228 | 1.577030166 |
| pyridoxate | 0.0029965 | 0.03474228 | 1.726378398 |
| isovalerate | 0.0030217 | 0.03474228 | 1.606903069 |
| 2-octenoyl carnitine | 0.0031061 | 0.03474228 | 3.380672484 |
| stearidonate (18:4n3) | 0.0035305 | 0.03782216 | 1.67663468 |
| N-acetylmethionine | 0.0036319 | 0.03782216 | 1.914048452 |
| ribitol | 0.003858 | 0.03863438 | 1.618327303 |
| tryptophan | 0.0039658 | 0.03863438 | 1.340167824 |
| pyroglutamine* | 0.0041565 | 0.03922674 | 2.333499037 |
| tyrosine | 0.0045634 | 0.04176221 | 1.680247205 |
| hexanoylcarnitine | 0.0049201 | 0.04340465 | 1.872747518 |
| 5-aminovalerate | 0.0050303 | 0.04340465 | 2.143298037 |
| pantothenate | 0.0056102 | 0.04706354 | 1.588194973 |
| 3-hydroxyisobutyrate | 0.0060836 | 0.0484175 | 1.825598145 |
| tryptophan betaine | 0.0060923 | 0.0484175 | 2.593659134 |
| cis-aconitate | 0.0064131 | 0.04900097 | 1.630295329 |
| proline | 0.0064902 | 0.04900097 | 1.509420603 |

Fig. 16
A) i)
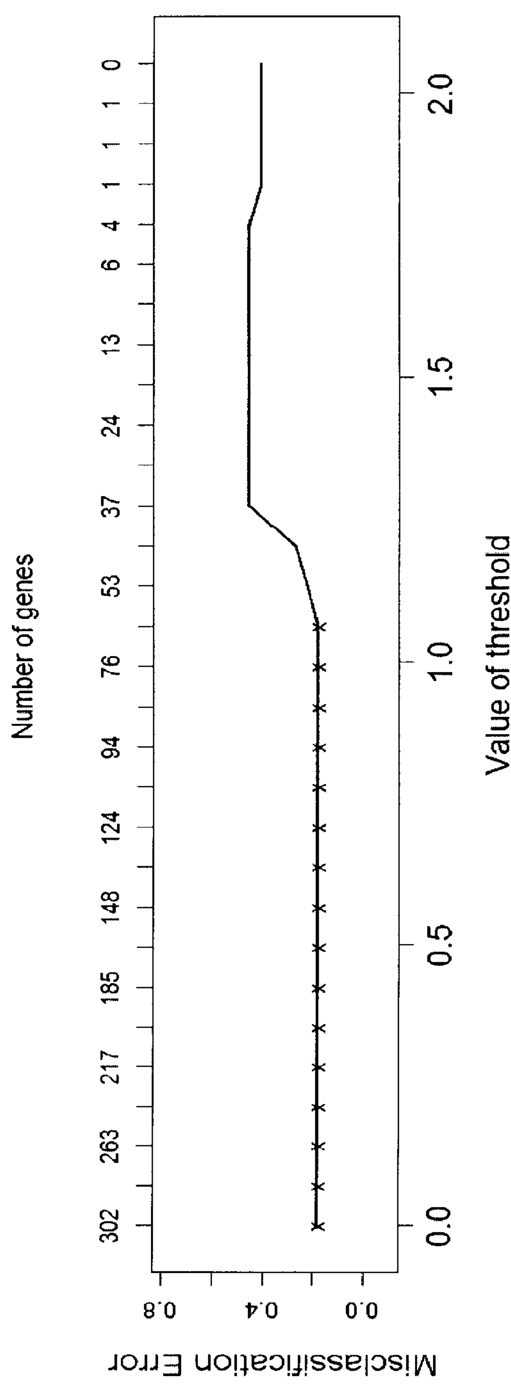
ii)
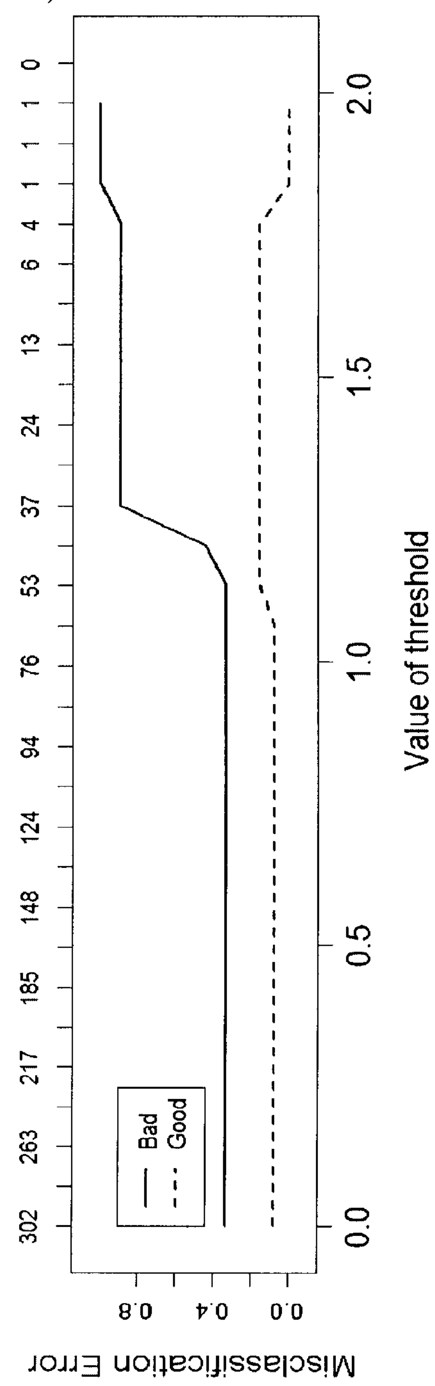

B)

DCD Start EVLP; Cross-validated sample probabilities from the nearest shrunken centroid classifier Fig. 16 (continued)

C)

DCD Start EVLP; List of 68 candidate metabolites

| ID | P.Value | adj.P.Val | FoldChange | prop-selected-in-CV |
|---|---|---|---|---|
| **5-aminovalerate** | **1.11E-05** | **0.00335271** | **3.43** | **1** |
| serine | 0.4831332 | 0.81238889 | 1.69 | 1 |
| **taurocholate** | **5.56E-05** | **0.00562692** | **6.15** | **1** |
| **glycocholate** | **5.59E-05** | **0.00562692** | **4.47** | **1** |
| mannitol | 0.9327775 | 0.96472189 | 2.61 | 1 |
| guanine | 0.0618738 | 0.44039806 | 2.51 | 1 |
| glutamate | 0.0317298 | 0.39926612 | 2.90 | 1 |
| stearidonate (18:4n3) | 0.0078595 | 0.16953995 | 1.60 | 1 |
| glycine | 0.5708339 | 0.84488433 | 1.64 | 1 |
| **histidine** | **0.0007537** | **0.04552173** | **3.19** | **1** |
| pyridoxate | 0.0014819 | 0.06393472 | 1.80 | 1 |
| urea | 0.0019215 | 0.07253831 | 44.81 | 1 |
| phosphoethanolamine | 0.3345784 | 0.75404975 | 1.93 | 1 |
| ascorbate (Vitamin C) | 0.2372687 | 0.64550701 | 3.28 | 1 |
| **betaine** | **0.0004735** | **0.03574886** | **1.84** | **1** |
| arginine | 0.7668742 | 0.92803136 | 1.50 | 1 |
| aspartate | 0.0263625 | 0.36265053 | 3.17 | 1 |
| 3-(4-hydroxyphenyl)lactate | 0.2035664 | 0.64204559 | 1.58 | 1 |
| 3-methyl-2-oxobutyrate | 0.0134075 | 0.22494855 | 1.44 | 1 |
| guanosine | 0.0094462 | 0.17861231 | 2.20 | 1 |
| sorbitol | 0.0627057 | 0.44039806 | 1.97 | 0.888888889 |
| pro-hydroxy-pro | 0.0039613 | 0.10875455 | 1.60 | 1 |
| alpha-hydroxyisocaproate | 0.1234135 | 0.51055992 | 1.57 | 1 |
| 2-hydroxybutyrate (AHB) | 0.0050039 | 0.12570802 | 1.75 | 1 |
| 2-aminobutyrate | 0.0446247 | 0.42732176 | 1.98 | 1 |
| 5,6-dihydrouracil | 0.1258472 | 0.51359264 | 1.59 | 1 |
| uracil | 0.0405995 | 0.42732176 | 1.82 | 0.888888889 |
| isobutyrylcarnitine | 0.0094629 | 0.17861231 | 1.99 | 0.888888889 |
| N-acetylneuraminate | 0.0531157 | 0.42732176 | 2.61 | 0.888888889 |
| butyrylcarnitine | 0.2403036 | 0.64550701 | 1.37 | 1 |
| alanine | 0.3766909 | 0.76379437 | 1.41 | 1 |
| pyroglutamine | 0.0030876 | 0.0932442 | 2.40 | 0.888888889 |
| malate | 0.102347 | 0.51055992 | 1.50 | 1 |
| propionylcarnitine | 0.0024487 | 0.082166 | 1.48 | 0.888888889 |
| lysine | 0.8563075 | 0.94474093 | 1.39 | 0.888888889 |
| 2-methylbutyroylcarnitine | 0.0104494 | 0.18563073 | 1.61 | 0.888888889 |
| deoxycarnitine | 0.0010416 | 0.05242607 | 1.60 | 0.888888889 |
| pipecolate | 0.0276191 | 0.36265053 | 1.65 | 0.888888889 |
| alpha-hydroxyisovalerate | 0.0373114 | 0.41733449 | 1.59 | 0.777777778 |
| asparagine | 0.654548 | 0.91093779 | 1.35 | 0.888888889 |
| carnitine | 0.0054113 | 0.12570802 | 1.46 | 1 |
| fucose | 0.1439035 | 0.56440055 | 1.92 | 0.888888889 |

Fig. 16 C (continued)

| ID | P.Value | adj.P.Val | FoldChange | prop-selected-in-CV |
|---|---|---|---|---|
| bilirubin (Z,Z) | 0.5422956 | 0.83350964 | 1.60 | 0.777777778 |
| methionine | 0.0733121 | 0.46125552 | 1.30 | 0.888888889 |
| 4-methyl-2-oxopentanoate | 0.053769 | 0.42732176 | 1.32 | 0.888888889 |
| docosapentaenoate (n6 DPA; 22:5n6) | 0.0356284 | 0.41383707 | 1.54 | 0.777777778 |
| isovalerylcarnitine | 0.1614728 | 0.60955978 | 1.45 | 0.777777778 |
| trans-4-hydroxyproline | 0.5233094 | 0.82708525 | 1.35 | 0.666666667 |
| ranitidine | 0.0838893 | 0.48807374 | 1.68 | 0.666666667 |
| ribose | 0.2470606 | 0.64916014 | 1.40 | 0.888888889 |
| gamma-glutamylleucine | 0.0974726 | 0.51055992 | 1.30 | 1 |
| 1-palmitoylglycerophosphoethanolamine | 0.0463432 | 0.42732176 | 1.42 | 0.777777778 |
| 3-hydroxyoctanoate | 0.4923005 | 0.81243035 | 1.44 | 0.888888889 |
| 7-alpha-hydroxy-3-oxo-4-cholestenoate (7-Hoca) | 0.3245307 | 0.73690436 | 1.31 | 0.777777778 |
| cytosine-2',3'-cyclic monophosphate | 0.0205639 | 0.31051545 | 1.61 | 0.777777778 |
| 3-hydroxybutyrate (BHBA) | 0.0795573 | 0.48052618 | 1.46 | 0.777777778 |
| cis-4-decenoyl carnitine | 0.1164834 | 0.51055992 | 1.46 | 0.555555556 |
| 3-methyl-2-oxovalerate | 0.0994927 | 0.51055992 | 1.31 | 0.777777778 |
| pantothenate | 0.0672295 | 0.44976627 | 1.35 | 0.666666667 |
| N-acetylmethionine | 0.2338415 | 0.64550701 | 1.30 | 0.777777778 |
| isoleucine | 0.1043899 | 0.51055992 | 1.28 | 0.777777778 |
| tyrosine | 0.2160145 | 0.64550701 | 1.25 | 0.777777778 |
| linolenate [alpha or gamma; (18:3n3 or 6)] | 0.0426004 | 0.42732176 | 1.62 | 0.777777778 |
| cysteine | 0.4210649 | 0.76669587 | 1.29 | 0.555555556 |
| 3-dehydrocarnitine | 0.0180918 | 0.28756457 | 1.57 | 0.666666667 |
| proline | 0.1505756 | 0.58299793 | 1.24 | 0.666666667 |
| N-acetylthreonine | 0.4199989 | 0.76669587 | 1.26 | 0.444444444 |
| xylitol | 0.3483263 | 0.76086309 | 1.35 | 0.666666667 |

Fig. 17
A) i)
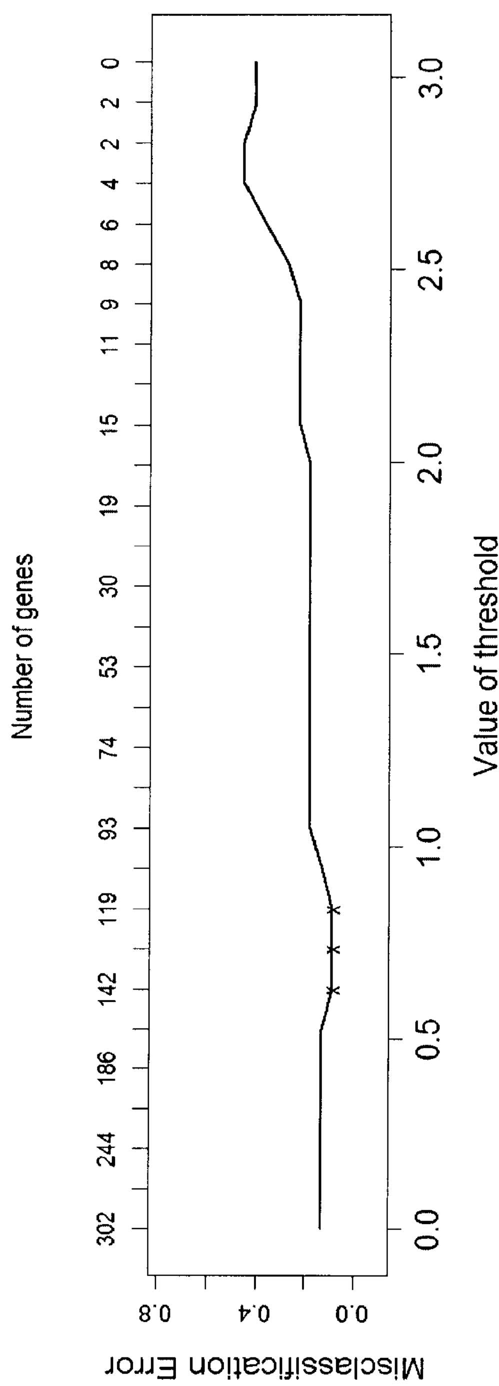
ii)
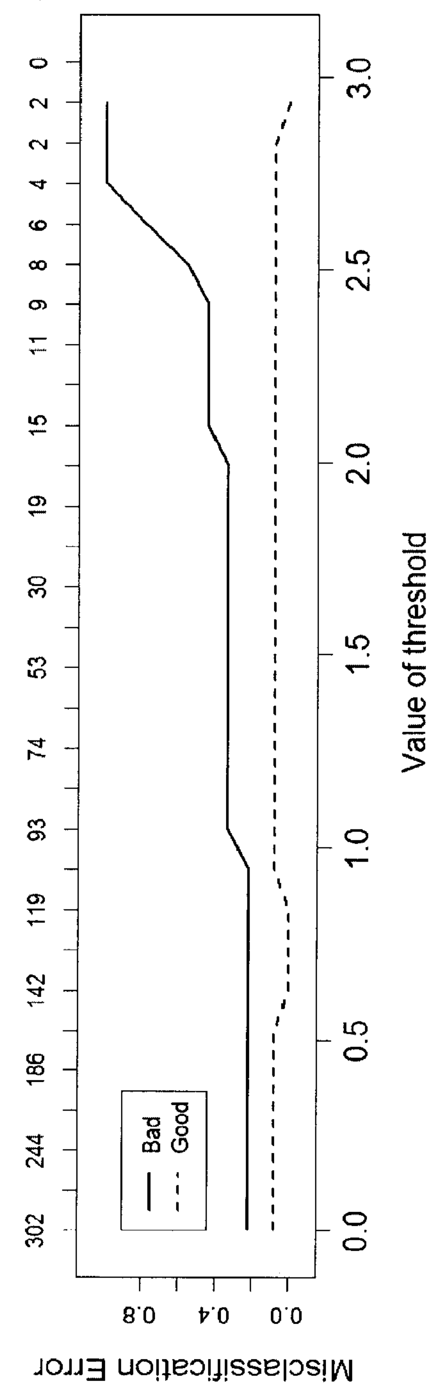

Table of metabolites identified as differentially present in 4h perfusate samples from good outcome lungs and poor outcome lungs using PAM.

| ID | P.Value | adj.P.Val | FoldChange | prop-selected-in-CV |
|---|---|---|---|---|
| lysine | 0.154492 | 0.35345819 | 13.62 | 1 |
| cystine | 0.074409 | 0.23654369 | 4.23 | 1 |
| glycine | 0.057566 | 0.199827 | 5.29 | 1 |
| **2-aminoadipate** | **0.009168** | **0.05324748** | **6.54** | **1** |
| serine | 0.066639 | 0.21874897 | 3.99 | 1 |
| ornithine | 0.20805 | 0.44782085 | 2.58 | 1 |
| arginine | 0.146352 | 0.34090327 | 7.31 | 1 |
| **trans-4-hydroxyproline** | **0.001595** | **0.02993462** | **4.55** | **1** |
| **alanine** | **0.007823** | **0.05324748** | **2.89** | **1** |
| **fucose** | **0.008828** | **0.05324748** | **3.27** | **1** |
| butyrylcarnitine | 0.014859 | 0.07605865 | 1.95 | 1 |
| **3-(4-hydroxyphenyl)lactate** | **0.008393** | **0.05324748** | **2.62** | **1** |
| phosphoethanolamine | 0.168427 | 0.37400648 | 2.55 | 0.555555556 |
| **xylitol** | **0.007659** | **0.05324748** | **2.38** | **1** |
| **alpha-hydroxyisocaproate** | **0.000216** | **0.01170798** | **3.03** | **0.888888889** |
| **N-acetylneuraminate** | **4.10E-05** | **0.00618932** | **8.24** | **0.777777778** |

Final list of Candidate Metabolites that distinguish between Good Lungs vs Bad lungs in DCD lung EVLP Perfusate taken at the start of EVLP

| ID | P.Value | adj.P.Val | FoldChange | prop-selected-in-CV |
|---|---|---|---|---|
| 5-aminovalerate | 1.11E-05 | 0.00335271 | 3.43 | 1 |
| taurocholate | 5.56E-05 | 0.00562692 | 6.15 | 1 |
| glycocholate | 5.59E-05 | 0.00562692 | 4.47 | 1 |
| histidine | 0.0007537 | 0.04552173 | 3.19 | 1 |
| betaine | 0.0004735 | 0.03574886 | 1.84 | 1 |

Final list of Candidate Metabolites that distinguish between Good Lungs vs Bad Lungs in DCD lung EVLP perfusate taken at the end of EVLP.

| ID | P.Value | adj.P.Val | FoldChange | prop-selected-in-CV |
|---|---|---|---|---|
| 2-aminoadipate | 0.009168 | 0.05324748 | 6.54 | 1 |
| trans-4-hydroxyproline | 0.001595 | 0.02993462 | 4.55 | 1 |
| alanine | 0.007823 | 0.05324748 | 2.89 | 1 |
| fucose | 0.008828 | 0.05324748 | 3.27 | 1 |
| 3-(4-hydroxyphenyl)lactate | 0.008393 | 0.05324748 | 2.62 | 1 |
| xylitol | 0.007659 | 0.05324748 | 2.38 | 1 |
| alpha-hydroxyisocaproate | 0.000216 | 0.01170798 | 3.03 | 0.888888889 |
| N-acetylneuraminate | 4.10E-05 | 0.00618932 | 8.24 | 0.777777778 |

Area Under the Curve plot for Candidate Metabolites in distinguishing between Good Lungs vs Bad Lungs using DCD Lung EVLP perfusate. Solid line for Start of EVLP and dashed line for End of EVLP.

METHODS AND COMPOSITIONS FOR ASSESSING LUNG GRAFTS

CROSS-REFERENCE TO RELATED APPLICATIONS

This application is a national phase entry of PCT/CA2014/000138, filed Feb. 20, 2014, which claims priority from U.S. Provisional patent application Ser. No. 61/766,862 filed Feb. 20, 2013; each of these applications being incorporated herein in their entirety by reference.

FIELD

The disclosure pertains to methods of assessing lung grafts, for example lung grafts that have been submitted to Ex-Vivo Lung Perfusion, for determining suitability for transplant.

BACKGROUND

Major obstacles for lung transplantation. Lung transplantation has become the mainstay of therapy for most end-stage lung diseases. However, the number of patients on the waiting list exceeds the number of organs available (1). More than 80% of donor lungs are potentially injured and therefore not considered suitable for transplantation. Furthermore, when a lung is found suitable for transplantation, the recipient may suffer from Primary Graft Dysfunction (PGD). PGD affects up to 25% of all lung transplant procedures. Currently there is no proven preventive therapy. PGD arises in the acute phase following lung transplantation and is characterized by significant deterioration of gas exchange and chest X-ray infiltrate. This condition is known not only for its contribution to early mortality but also for its impact on mid- and long-term survival (acute and chronic graft dysfunction) (2-4).

Clinical Trial of Ex-Vivo Lung Perfusion. With the use of normothermic ex vivo lung perfusion (EVLP), the retrieved donor lung can be perfused in an ex vivo circuit, providing an opportunity to reassess its function before transplantation. The first prospective clinical trial of EVLP has been performed, demonstrating the safety of the procedure (5). In this study, EVLP was applied to high-risk donor lungs which are often rejected for transplantation due to fear of PGD and compared results with a conventional lung transplantation group. It was shown that PGD occurrence was not statistically different. Thus, it was shown that EVLP expands the donor pool through the use of marginal lungs. Even though the percentage of PGD occurrence after EVLP tended to be lower compared to conventional lung transplantation, the number of lungs that developed PGD after EVLP is not zero (5). Analysis of these lungs showing poor results could be the key for future targeted treatment strategies to improve the rate of utilization of lung and post-operative outcomes.

SUMMARY

An aspect of the disclosure includes a method of classifying a lung graft subjected to normothermic ex vivo lung perfusion (EVLP), before perfusion, during perfusion and/or after perfusion, the method comprising:

a. collecting a test sample from the lung graft;
b. measuring a polypeptide level of a negative transplant predictor gene product selected from cytokine, chemokine, growth factor (CCG) predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1 in the test sample and/or determining a metabolite profile of the test sample for lung grafts that are from donors where the death was due to cardiac death (DCD);
c. identifying the graft as a good candidate for transplant or a poor candidate for transplant wherein an increased polypeptide level of one or more negative transplant outcome predictor gene products compared to an outcome control or metabolite profile most similar to a reference metabolic profile associated with poor outcome is indicative that the graft is a poor candidate for transplant.

In an embodiment, the test sample is a test donor lung tissue sample such as a biopsy, taken before, during or after EVLP.

In yet another embodiment, the test sample is a test bronchoalveolar lavage (BAL) sample.

In an embodiment, the test sample is a test perfusate sample collected during or after EVLP.

Another aspect of the disclosure includes a method of classifying a lung graft subjected to normothermic ex vivo lung perfusion (EVLP), during perfusion and/or after perfusion, the method comprising:

a. collecting a perfusate sample from the lung graft;
b. measuring a polypeptide level of a negative transplant predictor gene product selected from cytokine, chemokine, growth factor (CCG) predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1 in the test perfusate sample and/or determining a metabolite profile of the test perfusate sample for lung grafts that are from DCD donors;
c. identifying the graft as a good candidate for transplant or a poor candidate for transplant wherein an increased polypeptide level of one or more negative transplant outcome predictor gene products compared to an outcome control or metabolite profile most similar to a reference metabolic profile associated with poor outcome is indicative that the graft is a poor candidate for transplant.

In an embodiment, the negative transplant predictor gene product measured in a graft is from a high risk donor after brain death (DBD) or a DCD donor.

In an embodiment, the test perfusate sample is collected during or after EVLP.

In an embodiment, the CCG predictor gene product is M-CSF.

In another embodiment, the test perfusate sample is taken after about 30 minutes, or after about 1 hour of EVLP.

In an embodiment, the test perfusate sample is collected after about 1 hour of EVLP, 2 hours of EVLP, 3 hours of EVLP or 4 hours of EVLP.

In another embodiment, the graft undergoes EVLP for at least or about 4 hours, optionally 4 to 6 hours.

In a further embodiment, the negative transplant predictor gene product is a CCG predictor gene product.

In an embodiment, the M-CSF polypeptide is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of M-CSF polypeptide after 1 hour of EVLP is greater than about 30 pg/mL, 31 pg/mL, 32 pg/mL, 33 pg/mL, 34 pg/mL, 35 pg/mL, 36 pg/mL or 37 pg/mL.

In a further embodiment, the CCG predictor gene product is IL-8.

In another embodiment, the IL-8 polypeptide is increased at least 1.5×, 2×, 3×, 4×, 5×, 6×, 7×, 8×, 9× or 10× compared to the outcome control.

In an embodiment, the lung graft is identified as a poor candidate for transplant if the level of IL-8 polypeptide after 1 hour of EVLP is greater than about 70 pg/mL, 72 pg/mL, 74 pg/mL, 76 pg/mL, 80 pg/mL, 82 pg/mL, 84 pg/mL or 86 pg/mL.

Further, in an embodiment, the IL-8 polypeptide is increased at least 1.5×, 2×, 2.5×, 3×, 3.5× or 4×, compared to the outcome control.

In an embodiment, the lung graft is identified as a poor candidate for transplant if the level of IL-8 polypeptide after 4 hours of EVLP is greater than about 2000 pg/mL, 2250 pg/mL, 2500 pg/mL, 2750 pg/mL, 3000 pg/mL, 3250 pg/mL, 3500 pg/mL or 3750 pg/mL.

In an embodiment, the CCG predictor gene product is SCGF-beta.

In another embodiment, the SCGF-beta polypeptide is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of SCGF-beta polypeptide level after 1 hour of EVLP is greater than about 280 pg/mL, 290 pg/mL, 300 pg/mL, 310 pg/mL, 320 pg/mL, 330 pg/mL, 340 pg/mL or 350 pg/mL.

In an embodiment, the CCG predictor gene product is GRO-alpha.

In another embodiment, the GRO-alpha polypeptide is increased at least 1.5×, 2×, 2.5×, 3×, 3.5× or 4× compared to the outcome control.

In an embodiment, the lung graft is identified as a poor candidate for transplant if the level of GRO-alpha polypeptide level after 4 hours of EVLP is greater than about 550 pg/mL, 600 pg/mL, 650 pg/mL, 700 pg/mL, 750 pg/mL, 800 pg/mL, 850 pg/mL or 900 pg/mL.

In an embodiment, the CCG predictor gene product is G-CSF.

In an embodiment, the GRO-alpha polypeptide is increased at least 1.2×, 1.3×, 1.4×, 1.5×, 1.6×, 1.7×, 1.8×, 1.9× or 2× compared to the outcome control.

In a further embodiment, the lung graft is identified as a poor candidate for transplant if the level of G-CSF polypeptide level after 4 hours of EVLP is greater than about 3500 pg/mL, 4000 pg/mL, 4500 pg/mL, 5000 pg/mL, 5500 pg/mL, 6000 pg/mL, 6500 pg/mL or 7000 pg/mL.

In an embodiment, the CCG predictor gene product is MIP-1alpha.

In another embodiment, the MIP-1alpha polypeptide is increased at least 1.5×, 2×, 2.5×, 3×, 3.5× or 4× compared to the outcome control.

In an embodiment, the lung graft is identified as a poor candidate for transplant if the level of MIP-1alpha polypeptide level after 4 hours of EVLP is greater than about 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL or 85 pg/mL.

In an embodiment, the CCG predictor gene product is MIP-1 beta.

In an embodiment, the MIP-1 beta polypeptide is increased at least 1.5×, 2×, 2.5×, 3×, 3.5× or 4× compared to the outcome control.

In yet another embodiment, the lung graft is identified as a poor candidate for transplant if the level of MIP-1beta polypeptide level after 4 hours of EVLP is greater than about 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL or 85 pg/mL.

In another embodiment, the lung graft is identified as a poor candidate for transplant if the level of MIP-1 beta polypeptide level after 4 hours of EVLP is greater than about 1000 pg/mL, 1500 pg/mL, 2000 pg/mL, 2500 pg/mL, 3000 pg/mL, 3500 pg/mL, 4000 pg/mL or 4500 pg/mL.

In an embodiment, the levels of one or more of M-CSF, IL-8, SCGF-beta, GRO-alpha, G-CSF, MIP-1 alpha and/or MIP-1beta is assayed using multiplex assays such as Bio-plex Pro™ Human cytokine 27-plex Assay and Bio-plex Pro™ Human Cytokine 21-plex Assay.

In an embodiment, the endothelin predictor gene product is ET-1.

In an embodiment, the ET-1a polypeptide is increased at least 1.2×, 1.3×, 1.4×, 1.5×, 1.6×, 1.7×, 1.8×, 1.9× or 2× compared to the outcome control.

In a further embodiment, the lung graft is identified as a poor candidate for transplant if the level of ET-1 polypeptide level after 1 hour of EVLP is greater than about 2 pg/mL, 2.2 pg/mL, 2.4 pg/mL, 2.6 pg/mL, 2.8 pg/mL, 3 pg/mL, 3.1 pg/mL or 3.2 pg/mL.

In an embodiment, the lung graft is identified as a poor candidate for transplant if the level of ET-1 polypeptide level after 4 hours of EVLP is greater than about 1.5 pg/mL, 1.7 pg/mL, 1.9 pg/mL, 2.1 pg/mL, 2.3 pg/mL, 2.5 pg/mL, 2.7 pg/mL or 2.9 pg/mL.

In an embodiment, the endothelin predictor gene product is big ET-1.

In an embodiment, the big ET-1 polypeptide is increased at least 1.2×, 1.3×, 1.4×, 1.5×, 1.6×, 1.7×, 1.8×, 1.9× or 2× compared to the outcome control.

In another embodiment, the lung graft is identified as a poor candidate for transplant if the level of big ET-1 polypeptide level after 1 hour of EVLP is greater than about 8 pg/mL, 9 pg/mL, 10 pg/mL, 11 pg/mL, 12 pg/mL, 13 pg/mL, 14 pg/mL or 15 pg/mL.

In an embodiment, the lung graft is identified as a poor candidate for transplant if the level of big ET-1 polypeptide level after 4 hours of EVLP is greater than about 20 pg/mL, 22 pg/mL, 24 pg/mL, 26 pg/mL, 28 pg/mL, 30 pg/mL, 32 pg/mL or 34 pg/mL.

In an embodiment, the lung graft is from a DCD donor.

In an embodiment, the apoptosis predictor gene product is caspase cleaved CK18 and/or caspase 3.

In an embodiment, the level of caspase cleaved CK18 is increased at least 1.2×, 1.3×, 1.4×, 1.5×, 1.6×, 1.7×, 1.8×, 1.9× or 2× compared to the outcome control.

In another embodiment, the lung graft is identified as a poor candidate for transplant if the level of caspase cleaved CK18 polypeptide level after 4 hours of EVLP is greater than about 80 U/L, 84 U/L, 88 U/L, 92 U/L, 96 U/L or 100 U/L.

In an embodiment, the negative transplant outcome predictor gene product is HMGB-1.

In an embodiment, the level of HMGB-1 polypeptide is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of HMGB-1 polypeptide level after 4 hours of EVLP is greater than 14 ng/mL, 15.6 ng/mL, 20 ng/mL, 25 ng/mL, 30 ng/mL, 35 ng/mL, 40 ng/mL, 50 ng/mL, 60 ng/mL, 70 ng/mL, 80 ng/mL or 90 ng/mL.

In an embodiment, the level of the negative transplant predictor is detected using an ET-1 detection antibody, a big ET-1 detection antibody, an HMGB-1 detection antibody, M30 kit and/or a M65 kit.

In an embodiment, the metabolite profile comprises for each metabolite of one or more metabolites selected from metabolites listed in FIGS. 14, 15, 16C, 17C, 18A and/or 18C, at least one value corresponding to its level in the test perfusate sample.

In an embodiment, the one or more metabolites comprises at least 2, 3, 4 or 5 metabolites.

In an embodiment, the one or more metabolites comprises at least 6, 7, 8, 9 or 10 metabolites.

In yet another embodiment, the one or more metabolites comprise metabolites with a fold increase of at least 2 fold.

In an embodiment, the one or more metabolites comprises metabolites in any one of FIG. 14, 15, 16C, 17C, 18A or 18C with a p value of at least 0.05.

In an embodiment, the metabolite profile is determined using liquid chromatography and/or mass spectrometry.

In a further embodiment, the metabolite profile is determined using ultrahigh performance liquid chromatography/tandem mass spectrometry (UHPLC/MS/MS2) or gas chromatography/mass spectrometry (GC/MS).

In an embodiment, the UHPC/MS/MS2 is optimized for basic species or acidic species.

In an embodiment, the metabolites present in a test perfusate sample are identified by automated comparison of ion features in the experimental samples to a reference library of chemical standard entries that include retention time, molecular (m/Z) preferred adducts, and/or in source fragments and associated MS spectra.

In an embodiment, the identifying if the lung graft is a good candidate or a poor candidate for transplant comprises the use of linear models for microarray data (LIMMA) ANOVA-type classification method.

In a further embodiment, the identifying if the lung graft is a good candidate or a poor candidate for transplant comprises the use of a Prediction Analysis of Microarray (PAM) classification method.

In an embodiment, the identifying if the lung graft is a good candidate or a poor candidate for transplant comprises determining the metabolite profile of the test perfusate sample, the metabolite profile comprising for each metabolite of one or more metabolites, at least one value corresponding to its level in the test perfusate sample and comparing the metabolite profile to one or more reference metabolic profiles and identifying the lung graft as a good candidate if the metabolite profile is most similar to a good outcome class reference metabolite profile and identifying the lung graft as a poor candidate if the metabolite profile is most similar to a poor outcome class reference metabolite profile.

In an embodiment, the test perfusate sample is taken at approximately 1 hour after EVLP and the metabolite profile comprises the level of one or more of the metabolites in FIG. 14 or FIG. 16C.

In an embodiment, the test perfusate sample is taken at approximately 4 hours after EVLP and the metabolite profile comprises the level of one or more of the metabolites in FIG. 15 or 17C.

In an embodiment, the test perfusate sample is taken at approximately 1 hour after EVLP and the metabolite profile comprises the level of one or more of the metabolites in FIG. 18A.

In an embodiment, the test perfusate sample is taken at approximately 4 hours after EVLP and the metabolite profile comprises the level of one or more of the metabolites in FIG. 18B.

In yet another embodiment, the reference metabolic profile comprises a standardized centroid value of the one or more metabolites for each of a good outcome class comprising metabolite levels for a plurality of good outcome lung grafts and a poor outcome class comprising metabolite levels for a plurality of poor outcome lung grafts, wherein the average intensity for each metabolite in each class is divided by the within-class standard deviation for that metabolite to provide a standardized centroid value for the one or more metabolites for each class.

In an embodiment, the comparing the metabolite profile to one or more reference metabolic profiles comprises determining a test perfusate sample centroid value for the test perfusate sample metabolite profile, comparing the test perfusate sample centroid value to each of the good outcome and poor outcome centroid values, wherein the class whose centroid value is closest to, in squared distance, to the test perfusate sample centroid value is the predicted outcome class for the test perfusate sample.

In an embodiment, the good outcome lung grafts are characterized as being suitable for clinical transplantation after EVLP and in the recipient after transplantation, being free from inducing death from graft-related causes within 30 days, PGD or Extra-Corporeal Life Support.

In an embodiment, the poor outcome lung grafts are characterized as being unsuitable for clinical transplantation after EVLP or, in the recipient after transplantation, inducing death from graft-related causes within 30 days, PGD or requiring Extra-Corporeal Life Support.

In an embodiment, the test perfusate is a fluid sample.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 5A is a graphic showing Endothelin-1 (ET-1) levels at 1 hour of EVLP. FIG. 5B is a graphic showing Big Endothelin-1 (Big ET-1) levels at 1 hour of EVLP.

FIG. 6A is a graphic showing ET-1 levels at 4 hours of EVLP. FIG. 6B is a graphic showing Big ET-1 levels at 4 hours of EVLP.

FIG. 7A is a graphic showing ET-1 levels in DCD. FIG. 7B is a graphic showing Big ET-1 levels in DCD.

In FIG. 8A, ET-1 has an accuracy of 88% to detect Declined lungs from donors after cardiac death. In FIG. 8B, accuracy of ET-1 to detect PGD3 lungs from donors after cardiac death is 91%.

FIG. 9: Is a series of groups showing ROC curve control vs. declined for big ET-1 at 4 hours of EVLP. In FIG. 9A, Big ET-1 has an accuracy of 92% to detect Declined lungs from donors after cardiac death. In FIG. 9B, accuracy of Big ET-1 to detect PGD3 lungs from donors after cardiac death is 96%

FIG. 12A: Is a Mann Whitney test illustrating that HMGB-1 was significantly higher in the PGD group at 4 h (p=0.028) but not at 1 h of EVLP. FIG. 12B: Is a Wilcoxon signed-rank test illustrating that HMGB-1 at 4 h of EVLP increased significantly compared to 1 h in the PGD group (p=0.016), but not in the Control group (p=0.20).

FIG. 13A: Is a ROC curve, with the Area Under the Curve (AUC) of M30 at 4 hours of EVLP equal to 0.83 (95% Cl: 0.63-1.031, p=0.027). If the cut-point of M30 at 4 hours EVLP is set as 92.2 U/L, sensitivity is 50% and specificity is 100%. (b): Is a ROC curve showing the AUC of HMGB-1 at 4 hours of EVLP was 0.85 (95% Cl: 0.65-1.05, p=0.024). If the cut-point of HMGB-1 at 4 hours EVLP is set as 15.6 ng/mL, sensitivity is 100% and specificity is 50%.

FIG. 14 describes metabolites that were identified as differentially present in 1 h test perfusate samples from good outcome lungs and poor outcome lungs using linear models for microarray data (LIMMA).

FIG. 15 describes metabolites that were identified as differentially present in 4 h test perfusate samples from good outcome lungs and poor outcome lungs using LIMMA.

FIG. 18A: A list of Candidate Metabolites that distinguish between Good Lungs vs. Bad lungs in DCD lung EVLP Test perfusate taken at the start of EVLP. FIG. 18B: A list of Candidate Metabolites that distinguish between Good Lungs vs. Bad Lungs in DCD lung EVLP test perfusate taken at the end of EVLP.

DETAILED DESCRIPTION OF THE DISCLOSURE

I. Definitions

Figure 1:
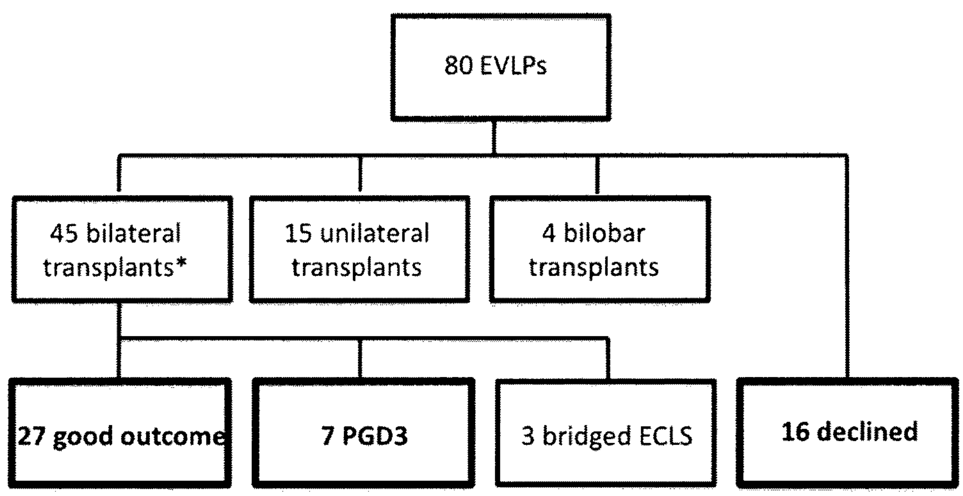
FIG. 1: Is a schematic of the study design of the Human Ex Vivo Lung Perfusion (HELP) trial.

The term "a negative transplant predictor gene product" refers to a biomarker whose increased expression in EVLP test perfusate is associated with poor outcome after transplant, and includes 1) CCG predictor gene products M-CSF, IL-8, SCGF-beta, G-CSF, GRO-alpha, G-CSF, MIP-1alpha, and/or MIP-1beta, 2) endothelin predictor gene products endothelin 1 (ET-1) and/or big ET-1, and/or 3) apoptosis predictor gene products cytokeratin 18 (CK-18), caspase 3 and/or HMGB-1.

The term "CCG predictor gene products" as used herein is used to refer to M-CSF, IL-8, SCGF-beta, GRO-alpha, G-CSF, MIP-1 alpha, and/or MIP-1beta, and optionally other CSF, such as GM-CSF.

The term "M-CSF" as used herein means macrophage stimulating factor which is a secreted cytokine, and includes all naturally occurring forms, for example from all species, and particularly human including, for example, human M-CSF which has amino acid sequence accession #AAC08707, herein incorporated by reference.

The term "IL-8" as used herein means interleukin-8 which is a secreted cytokine, and includes all naturally occurring forms, for example from all species and particularly human including for example human IL-8 which has amino acid sequence accession #CAA32622, herein incorporated by reference.

The term "SCGF-beta" as used herein means "Stem Cell Growth Factor-beta" and includes all naturally occurring forms, for example from all species, and particularly human including for example human SCGF-beta which has amino acid sequence accession #BAA21499, herein incorporated by reference.

The term "GRO-alpha" as used herein as used herein means "Growth-Regulated Oncogene-alpha" and includes all naturally occurring forms, for example from all species, and particularly human including for example human GRO-alpha which has amino acid sequence accession #AAH11976, herein incorporated by reference.

The term "G-CSF" as used herein means granulocyte stimulating factor which is a secreted cytokine, and includes all naturally occurring forms, for example from all species, and particularly human including, for example, human G-CSF which has amino acid sequence accession #ACF41164, herein incorporated by reference.

The term "MIP-1alpha" as used herein means macrophage inflammatory protein 1 alpha and includes all naturally occurring forms, for example from all species, and particularly human including for example human MIP-1alpha which has amino acid sequence accession #AAI71891, herein incorporated by reference.

The term "MIP-1beta" as used herein means macrophage inflammatory protein 1 beta and includes all naturally occurring forms, for example from all species, and particularly human including for example human MIP-1beta which has amino acid sequence accession #AAI04228, herein incorporated by reference.

The term "Endothelin predictor gene products" as used herein is used to refer to ET-1 and/or big ET-1.

The term "ET-1" as used herein means endothelin-1 which is a vasoconstrictive peptide typically about 21 amino acids, and includes all naturally occurring forms, for example from all species, and particularly human including for example human ET-1 which has amino acid sequence accession #AAA52339, herein incorporated by reference.

The term "big ET-1" as used herein means the precursor product of ET-1, which is typically 38 amino acids, and includes all naturally occurring forms, for example from all species, and particularly human including for example human big ET-1 which has amino acid sequence accession #P05305, herein incorporated by reference.

The term "apoptosis predictor gene products" as used herein is used to refer to CK-18, including caspase cleaved fragments thereof, caspase-3, and/or HMGB-1.

The term "CK-18" as used herein means cytokeratin-18 and fragments thereof for example caspase cleaved fragments and includes all naturally occurring forms, for example from all species, and particularly human including for example human CK-18 which has amino acid sequence accession #CAA31375, herein incorporated by reference.

The term "caspase 3" as used herein is an apoptotic enzyme and Includes all naturally occurring forms, for example from all species, and particularly human including for example human caspase 3 which has amino acid sequence accession #CAC88866 herein incorporated by reference.

The term "HMGB-1" as used herein means high mobility group protein B1 also known as high mobility group protein 1 (HMG-1) and amphoterin is a protein product of HMGB-1 gene and includes all naturally occurring forms, for example from all species, and particularly human including for example human HMGB-1 which has amino acid sequence accession #CAG33144, herein incorporated by reference.

The term "metabolite profile" as used herein means for each of one or more metabolites selected from metabolites listed in FIGS. 14, 15, 16C, 17C, 18A and/or 18B as least one value associated with its level in a test sample such as a perfusate sample, optionally an average of multiple levels (e.g. repeat samples), which can for example be used to assess whether a lung graft is suitable for transplant by comparing to a reference metabolite profile which is determined from good outcome lung grafts and/or bad outcome lung grafts. The metabolite profile can be used to calculate a risk score and compared to a threshold value, above or below which is indicative of whether the lung graft is a poor or good candidate for transplant.

A "reference metabolite profile" as used herein refers to the level signature of a one or more metabolites (e.g. at least 2), whose level is associated with transplant suitability. The reference metabolite profile can be determined using two or more or a plurality of known outcome lung grafts, wherein the metabolite profile is similar between reference lungs with a similar outcome thereby defining an outcome class and is different to other reference metabolite profiles in a different outcome class. The reference metabolite profile comprises for example, levels such as averages or centroid values for 2 or more, 3 or more, 4 or more or 5 or more metabolites selected from those listed in FIGS. 14, 15, 16C, 17C, 18A and/or 18B. A reference metabolite profile associated with good outcome lungs can be referred to a good outcome reference metabolite profile and a reference metabolite profile associated with poor outcome lungs can be referred to as a poor outcome reference profile.

The term "classifying" as used herein refers to assigning, to a class or kind, an unclassified item. A "class" or "group" then being a grouping of items, based on one or more characteristics, attributes, properties, qualities, effects, parameters, etc., which they have in common, for the purpose of classifying them according to an established system or scheme. For example, subjects having increased expression of one or more negative transplant predictor gene products are predicted to have poor suitability for lung transplant. Similarly the metabolite profile can for example be used to calculate a risk score to classify the subject, for example subjects having a summed expression value (e.g. lung graft risk score) above a selected threshold which can for example be the median score of a plurality of lungs.

The term "death due to cardiac death" or "DCD" as used herein means the withdrawal of life support of a patient after it has been determined that there is no long-term prognosis for recovery, and subjects who experience cardiocirculatory arrest and a qualified decision is made to terminate or not initiate resuscitation. A DCD lung graft is accordingly a lung graft obtained from such a patient.

The term "donation after brain death" or "DBD" as used herein means donors who experience the irreversible end of all brain activity but whose body, including transplantable organs, are maintained through external mechanical means.

The term "outcome control" as used herein refers to a control graft with known outcome and/or a predetermined threshold based on a plurality of known outcome grafts, above which threshold a graft is identified as a poor candidate and below which (and/or comparable to) a candidate is identified as suitable for transplant. The threshold value can for example for each of the one or more polypeptide biomarkers, be determined from the levels of the biomarkers in a plurality of known outcome lungs. For example, the optimal and/or acceptable threshold is selected based on the one or more levels of biomarkers. The outcome control can also be a comparator lung with known outcome as described in the examples. A person skilled in the art would understand that a decreased and/or comparable polypeptide level of one or more negative transplant outcome predictor gene products compared to the outcome control can be identified as a good candidate. The outcome control can for example be a good outcome control or a poor outcome control. A person skilled in the art will appreciate that the difference in the amount of a polypeptide level measured for example as an antibody-antigen complex, indicative of lung graft suitable for transplant and one that is not, will vary depending on the type of outcome control. For example, if the outcome control is obtained from or a value determined from lungs known to be good outcome lung grafts, then less or comparable measurable antibody-antigen complex in the test sample, optionally test perfusate sample as compared to the good outcome control indicates that the lung graft is suitable for transplant.

If the control is obtained from or a value determined from lungs known to be good outcome lung grafts, then greater measurable antibody-antigen complex in the test sample as compared to the good outcome control indicates that the lung graft is not suitable for transplant. Alternatively, if for example the outcome control is obtained from or a value determined from lungs known to be poor outcome lung grafts, then less measurable antibody-antigen complex in the test sample as compared to the poor outcome control indicates that the lung graft is suitable for transplant. If the control is obtained from or a value determined from lungs known to be poor outcome lung grafts, then equal or greater measurable antibody-antigen complex in the test sample as compared to the poor outcome control indicates that the lung graft is not suitable for transplant.

The term "good outcome lung grafts" as used herein means lung grafts that are predicted to be and/or which are characterized as being suitable for clinical transplantation after EVLP and in the recipient after transplantation, being free from inducing death from graft-related causes within 30 days, PGD or Extra-Corporeal Life Support.

The term "poor outcome lung grafts" used herein means lung grafts that are predicted to be and/or which are characterized as being unsuitable for clinical transplantation after EVLP or, in the recipient after transplantation, inducing death from graft-related causes within 30 days, PGD or requiring Extra-Corporeal Life Support. A lung graft is characterized as being unsuitable for clinical transplant after EVLP for example after visual and physiologic examination such as when gas exchange function is not acceptable represented by a partial pressure of oxygen less than 350 mmHg with a fraction of inspired oxygen of 100%; or 15% worsening of lung compliance compared to 1 h EVLP; or 15% worsening of pulmonary vascular resistance compared to 1 h EVLP; or worsening of ex vivo x-ray. The assessment of suitability for transplant requires significant skill and experience. Biomarkers that are able to predict suitability can provide a more accessible quantitative benchmark for use in assessing transplant suitability.

The term "most similar" as used herein in the context of a reference metabolite profile refers to a reference metabolite profile (e.g. good outcome reference metabolite profile or poor outcome reference metabolite profile) that shows the greatest number of identities and/or degree of changes with the lung graft metabolite profile.

The term "perfusate sample" as used herein means an aliquot of a perfusion solution such as Steen Solution™ that can be used for EVLP and which is taken subsequent to starting EVLP, optionally at time of fluid replenishment. Typically perfusate samples are snap frozen. The sample can for example be purified and/or treated prior to assessment.

The term "Steen Solution™" as used herein means a buffered dextran containing extracellular-type solution with an optimized colloid osmotic pressure developed specifically for EVLP, containing Human Serum Albumin, Dextran and extra-cellular electrolyte composition (lowK+).

The term "declined lungs" as used herein means lungs that after EVLP were declined for transplant. Lungs are declined for example if gas exchange function is not acceptable, represented by a partial pressure of oxygen less than 350 mmHg with a fraction of inspired oxygen of 100%; or 15% worsening of lung compliance compared to 1 h EVLP; or 15% worsening of pulmonary vascular resistance compared to 1 h EVLP; or worsening of ex vivo x-ray.

The term "suitability for transplant" as used herein means an organ that is predicted to be a good outcome lung graft.

The term "PGD3" as used herein means Primary Graft Dysfunction Grade 3, where the $PaO_2/FIO_2$ ratio is <200 and the chest x-ray shows diffuse allograft infiltrates.

The term "antibody" as used herein is intended to include monoclonal antibodies including chimeric and humanized monoclonal antibodies, polyclonal antibodies, humanized antibodies, human antibodies, and chimeric antibodies. The antibody may be from recombinant sources and/or produced in transgenic animals. The term "antibody fragment" as used herein is intended to include Fab, Fab', $F(ab')_2$, scFv, dsFv, ds-scFv, dimers, minibodies, diabodies, and multimers thereof and bispecific antibody fragments. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques. The antibodies are optionally in any useful isotype, including IgM which in one embodiment is used for diagnostic applications and/or IgG, such as IgG1, IgG2, IgG3 and IgG4.

The term "detection agent" refers to an agent (optionally a detection antibody) that selectively binds and is capable of binding its cognate biomarker compared to another molecule and which can be used to detect a level and/or the presence of the biomarker. A biomarker specific detection agent can include probes, primers and the like as well as binding polypeptides such as antibodies which can for example be used with immunohistochemistry (IHC), ELISA, immunofluorescence, radioimmunoassay, dot blotting, FACS and protein microarray to detect the expression level of a biomarker described herein. Similarly, "an antibody or fragment thereof" (e.g. binding fragment), that specifically binds a biomarker refers to an antibody or fragment that selectively binds its cognate biomarker compared to another molecule. "Selective" is used contextually, to characterize the binding properties of an antibody. An antibody that binds specifically or selectively to a given biomarker or epitope thereof will bind to that biomarker and/or epitope either with greater avidity or with more specificity, relative to other, different molecules. For example, the antibody can bind 3-5, 5-7, 7-10, 10-15, 5-15, or 5-30 fold more efficiently to its cognate biomarker compared to another molecule. The "detection agent" can for example be coupled to or labeled with a detectable marker. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The term "level" as used herein refers to an amount (e.g. relative amount or concentration) of biomarker (e.g. polypeptide or metabolite) that is detectable, measurable or quantifiable in a test biological sample and/or a reference biological sample. For example, the level can be a concentration such as μg/L or ng/L, or a relative amount such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 10, 15, 20, 25, and/or 30 times more or less than an outcome control biomarker or reference profile level. The outcome control biomarker polypeptide level can, for example, be the average or median level in a plurality of known outcome lungs.

The term "subject" as used herein includes all members of the animal kingdom including mammals, and suitably refers to humans.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods

Disclosed herein are polypeptide and metabolite biomarkers that can be used to assess whether a lung graft such as a marginal lung graft that is subjected to normothermic ex vivo lung perfusion (EVLP) is suitable for transplant.

The biomarkers include polypeptide biomarkers including 1) cytokine, chemokine, growth factor (CCG) predictor gene products M-CSF, IL-8, SCGF-beta, GRO-alpha, G-CSF, MIP-1 alpha, and/or MIP-1beta and optionally other CSF; 2) endothelin predictor gene products endothelin 1 (ET-1) and/or big ET-1; and/or 3) apoptosis predictor gene products cytokeratin 18 (CK-18), caspase 3 and/or HMGB-1, as well as metabolite biomarkers as listed for example in FIGS. 14, 15, 16C, 17C, 18A and 18B.

The polypeptide biomarkers are negative transplant predictor gene products and their increased expression in EVLP test perfusate is associated with poor outcome after transplant.

The metabolite biomarkers can be negative transplant predictors and their increased levels are associated with poor outcome. Some metabolite biomarkers are beneficial markers wherein an increased level is associated with good outcome. Comparing the metabolite profile to one or more reference profiles and identifying the reference metabolic profile (e.g. good or poor) most similar to the sample metabolic profile can provide an indication if the lung graft is a good or poor candidate for transplant.

Apoptosis is one type of cell death and is reported to occur during reperfusion of the transplanted lung (6). Moreover, apoptotic cells which express phosphatidylserine on the cell membrane induce attachment of neutrophils, lymphocytes, and platelets during reperfusion (7, 8). This causes microthrombus which in turn induces local hypoxia stress and infiltrating T-cells induce further apoptosis mediated by inflammatory cytokines (9). This may be an important mechanism of ischemia reperfusion injury and likely subsequent PGD. A caspase inhibitor application in a rat single transplant model has been demonstrated to diminish apoptotic cells at reperfusion period and improve post-transplant oxygenation (10).

Accordingly in an aspect, the disclosure includes a method of classifying a lung graft, subjected to normothermic ex vivo lung perfusion (EVLP), before perfusion, during perfusion and/or after perfusion, the method comprising:

a. collecting a test sample from the lung graft;

b. measuring a polypeptide level of a negative transplant predictor gene product selected from cytokine, chemokine, growth factor (CCG) predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1 in the test sample and/or determining a metabolite profile of the test sample for lung grafts that are from donors where the death was due to cardiac death (DCD);

c. identifying the graft as a good candidate for transplant or a poor candidate for transplant wherein an increased polypeptide level of one or more negative transplant outcome predictor gene products compared to an outcome control or metabolite profile most similar to a reference metabolic profile associated with poor outcome is indicative that the graft is a poor candidate for transplant.

In an embodiment, the test sample is a test donor lung tissue sample such as a biopsy, taken before, during or after EVLP. Where the sample is taken before subjecting the lung graft to EVLP, polypeptide levels and/or metabolite levels that are associated with good outcome after transplant, the lung graft may be subjected to EVLP and/or may be transplanted without EVLP.

In yet another embodiment, the test sample is a test bronchoalveolar lavage (BAL) sample. A BAL sample is for example taken by passing a bronchoscope into the lungs and squirting fluid into a small part of the lung which is then recollected for examination. An aliquot can be analysed for the biomarkers described herein. BAL can be used to determine the protein composition of the pulmonary airways.

In an embodiment, the test sample is a test perfusate sample collected during or after EVLP.

A perfusate sample is for example taken by taking during or after EVLP which involves pumping a nutrient solution such as Steen Solution™ through the blood vessels of the lungs while at the same time supplying them with oxygen from a ventilator machine.

The biomarkers described herein are secreted biomarkers which as described herein can be measured in perfusate samples. BAL samples would also be expected to comprise the secreted biomarkers. Furthermore, the secreted biomarkers can be increased in lung cells prior to release and donor lung tissue samples may also be assayed for the biomarkers disclosed.

In another aspect, the disclosure includes a method of classifying a lung graft subjected to normothermic ex vivo lung perfusion (EVLP), during perfusion and/or after perfusion, the method comprising:

a. collecting a test perfusate sample from the lung graft;
b. measuring a polypeptide level of a negative transplant predictor gene product selected from CCG predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1 in the test perfusate sample and/or determining a metabolite profile of the test perfusate sample for lung grafts that are from DCD donors;
c. identifying the graft as a good candidate for transplant or a poor candidate for transplant wherein an increased polypeptide level of one or more negative transplant outcome predictor gene products compared to an outcome control or metabolite profile most similar to a reference metabolic profile associated with poor outcome is indicative the graft is a poor candidate for transplant.

The outcome control can for example be a predetermined threshold, for example for one or more polypeptide biomarkers, determined from the levels of the biomarkers in a plurality of known outcome lungs. The outcome control can also be a comparator lung with known outcome as described in the examples. A person skilled in the art would understand that a decreased polypeptide level of one or more negative transplant outcome predictor gene products compared to the outcome control can be identified as a good candidate.

As demonstrated in the Examples, the polypeptide markers were increased in lung grafts from high risk DBDs and DCDs. In an embodiment, the graft is from a high risk DBD or a DCD.

Typically a lung graft receives EVLP for about 4-6 hours. It is demonstrated that 1 hour and 4 hour test perfusate sample can predict graft response after transplant. In an embodiment, the graft undergoes EVLP for at least 4 hours, optionally 4 to 6 hours.

In an embodiment, the perfusate sample is collected during or after EVLP, for example at points where perfusate fluid is removed from the circuit. During an EVLP assessment for example, the EVLP circuit can be primed with 2000 ml of Steen Solution™. Subsequently, the circulating Steen Solution™ within the EVLP circuit can be replenished in the following manner: at the end of the first hour, one litre of the perfusate is removed from the circuit, and one litre of fresh Steen Solution™ is replaced into the circuit. After this, at the end of each subsequent hour, 500 mL of perfusate fluid can be removed from the circuit, and 500 mL of fresh Steen Solution™ can be added to the circuit. As described below, at the end of the first hour of perfusion and at the end of four hours of perfusion, 10 mL aliquots of the test perfusate fluid were withdrawn from the perfusion circuit just before the replacement of perfusion fluid, and immediately frozen.

In an embodiment, the test perfusate sample is collected after 1 hour of EVLP, 2 hours of EVLP, 3 hours of EVLP or 4 hours of EVLP. Test perfusate samples can also be collected at other times for example, after 5 hours or 6 hours of EVLP.

In an embodiment, the negative transplant predictor gene product is a CCG predictor gene product. In an embodiment, the CCG predictor gene product is M-CSF.

It is demonstrated herein that M-CSF levels were increased at the one hour time point. Accordingly, in an embodiment the test perfusate sample is taken after about 30 minutes, or after 1 hour of EVLP.

In an embodiment, the M-CSF polypeptide is increased at least 1.2×, 1.3×, 1.4×, 1.5×, 1.6×, 1.7×, 1.8×, 1.9× or 2× compared to the outcome control.

The Examples also identify threshold levels that can be used to classify a lung. In an embodiment, the lung graft is identified as a poor candidate for transplant if the level of M-CSF polypeptide after 1 hour of EVLP is greater than 30 pg/mL, 31 pg/mL, 32 pg/mL, 33 pg/mL, 34 pg/mL, 35 pg/mL, 36 pg/mL or 37 pg/mL.

In another embodiment, the CCG predictor gene product is IL-8. In an embodiment, the test perfusate sample is taken after about 30 minutes, or after 1 hour of EVLP.

In an embodiment, the IL-8 polypeptide is increased at least 1.5×, 2×, 3×, 4×, 5×, 6×, 7×, 8×, 9× or 10× compared to the outcome control.

In an embodiment, the lung graft is identified as a poor candidate for transplant if the level of IL-8 polypeptide after 1 hour of EVLP is greater than 70 pg/mL, 72 pg/mL, 74 pg/mL, 76 pg/mL, 80 pg/mL, 82 pg/mL, 84 pg/mL or 86 pg/mL.

It is demonstrated that IL-8 is increased in the 4 hour time point. In an embodiment, the test perfusate sample is taken after about 1, 2, 3 or 4 hours of EVLP In an embodiment, the IL-8 polypeptide is increased at least 1.5×, 2×, 2.5×, 3×, 3.5× or 4× compared to the outcome control.

In an embodiment, the lung graft is identified as a poor candidate for transplant if the level of IL-8 polypeptide after 4 hours of EVLP is greater than 2000 pg/mL, 2250 pg/mL, 2500 pg/mL, 2750 pg/mL, 3000 pg/mL, 3250 pg/mL, 3500 pg/mL or 3750 pg/mL.

In a further embodiment, the CCG predictor gene product is SCGF-beta.

It is demonstrated that SCGF-beta is increased in the 1 hour time point analysed. In an embodiment, the test perfusate sample is taken after about 30 minutes, or after 1 hour of EVLP.

In an embodiment, the SCGF-beta polypeptide is increased at least 1.2×, 1.3×, 1.4×, 1.5×, 1.6×, 1.7×, 1.8×, 1.9× or 2× compared to the outcome control.

In an embodiment, the lung graft is identified as poor candidate for transplant if the level of SCGF-beta polypeptide level after 1 hour of EVLP is greater than 280 pg/mL, 290 pg/mL, 300 pg/mL, 310 pg/mL, 320 pg/mL, 330 pg/mL, 340 pg/mL or 350 pg/mL.

In another embodiment, the CCG predictor gene product is GRO-alpha.

It is demonstrated that GRO-alpha is increased in the 4 hour time point analysed. In an embodiment, the test perfusate sample is taken after about 1, 2, 3 or 4 hours of EVLP.

In an embodiment, the GRO-alpha polypeptide is increased at least 1.5×, 2×, 2.5×, 3×, 3.5× or 4× compared to the outcome control.

In an embodiment, the lung graft is identified as a poor candidate for transplant if the level of GRO-alpha polypeptide level after 4 hours of EVLP is greater than 550 pg/mL, 600 pg/mL, 650 pg/mL, 700 pg/mL, 750 pg/mL, 800 pg/mL, 850 pg/mL or 900 pg/mL.

In yet another embodiment, the CCG predictor gene product is G-CSF.

It is demonstrated that G-CSF is increased in the 4 hour time point analysed. In an embodiment, the test perfusate sample is taken after about 1, 2, 3 or 4 hours of EVLP.

In an embodiment, the G-CSF polypeptide is increased at least 1.2×, 1.3×, 1.4×, 1.5×, 1.6×, 1.7×, 1.8×, 1.9× or 2× compared to the outcome control.

In an embodiment, the lung graft is identified as poor candidate for transplant if the level of G-CSF polypeptide level after 4 hours of EVLP is greater than 3500 pg/mL, 4000 pg/mL, 4500 pg/mL, 5000 pg/mL, 5500 pg/mL, 6000 pg/mL, 6500 pg/mL or 7000 pg/mL.

Both M-CSF and G-CSF are demonstrated herein to be associated with lung graft suitability for transplant. Other CSF molecules such as GM-CSF are also expected to be useful.

In yet another embodiment, the CCG predictor gene product is MIP-1alpha.

In an embodiment, the test perfusate sample is taken after about 1, 2, 3 or 4 hours of EVLP.

In an embodiment, the MIP-1alpha polypeptide is increased at least 1.5×, 2×, 2.5×, 3×, 3.5× or 4× compared to the outcome control.

In an embodiment, the lung graft is identified as poor candidate for transplant if the level of MIP-1alpha polypeptide level after 4 hours of EVLP is greater than 30 pg/mL, 35 pg/mL, 40 pg/mL, 45 pg/mL, 50 pg/mL, 55 pg/mL, 60 pg/mL, 65 pg/mL, 70 pg/mL, 75 pg/mL, 80 pg/mL or 85 pg/mL.

In another embodiment, the CCG predictor gene product is MIP-1beta.

In an embodiment, the test perfusate sample is taken after about 1, 2, 3 or 4 hours of EVLP.

In an embodiment, the MIP-1 beta polypeptide is increased at least 1.5×, 2×, 2.5×, 3×, 3.5× or 4× compared to the outcome control.

In an embodiment, the lung graft is identified as a poor candidate for transplant if the level of MIP-1 beta polypeptide level after 4 hours of EVLP is greater than 1000 pg/mL, 1500 pg/mL, 2000 pg/mL, 2500 pg/mL, 3000 pg/mL, 3500 pg/mL, 4000 pg/mL or 4500 pg/mL.

The levels of the polypeptide biomarkers can be detected using a number of methods known in the art. For example, the methods can include immunoassays such as ELISA and multiplex assays, flow cytometry, Western blots, and immunoprecipitation followed by SDS-PAGE immunocytochemistry. Polypeptide microarrays can also be used.

In an embodiment, the levels of one or more of M-CSF, IL-8 SCGF-beta, GRO-alpha, G-CSF, MIP-1 alpha and/or MIP-1beta is assayed multiplex assays such as Bio-plex Pro™ Human cytokine 27-plex Assay and Bio-plex Pro™ Human Cytokine 21-plex Assay.

In another embodiment, the endothelin predictor gene product is ET-1.

In an embodiment, the test perfusate sample is taken after about 30 minutes or 1 hour of EVLP and/or after about 1, 2, 3 or 4 hours of EVLP.

In an embodiment, the ET-1a polypeptide is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of ET-1 polypeptide level after 1 hour of EVLP is greater than 2 pg/mL, 2.2 pg/mL, 2.4 pg/mL, 2.6 pg/mL, 2.8 pg/mL, 3 pg/mL, 3.1 pg/mL or 3.2 pg/mL.

In an embodiment, the lung graft is identified as a poor candidate for transplant if the level of ET-1 polypeptide level after 4 hours of EVLP is greater than 1.5 pg/mL, 1.7 pg/mL, 1.9 pg/mL, 2.1 pg/mL, 2.3 pg/mL, 2.5 pg/mL, 2.7 pg/mL or 2.9 pg/mL.

In another embodiment, the endothelin predictor gene product is big ET-1.

In an embodiment, the test perfusate sample is taken after about 30 minutes or 1 hour of EVLP.

In an embodiment, the big ET-1 polypeptide is increased at least 1.2×, 1.3×, 1.4×, 1.5×, 1.6×, 1.7×, 1.8×, 1.9× or 2× compared to the outcome control.

In an embodiment, the lung graft is identified as poor candidate for transplant if the level of big ET-1 polypeptide level after 1 hour of EVLP is greater than 8 pg/mL, 9 pg/mL, 10 pg/mL, 11 pg/mL, 12 pg/mL, 13 pg/mL, 14 pg/mL or 15 pg/mL.

In an embodiment, the lung graft is identified as a poor candidate for transplant if the level of big ET-1 polypeptide level after 4 hours of EVLP is greater than 20 pg/mL, 22 pg/mL, 24 pg/mL, 26 pg/mL, 28 pg/mL, 30 pg/mL, 32 pg/mL or 34 pg/mL.

In an embodiment, the apoptosis predictor gene product is caspase cleaved CK18. In an embodiment, the apoptosis predictor gene product is caspase 3.

In an embodiment, the test perfusate sample is taken after about 1, 2, 3 or 4 hours of EVLP.

In an embodiment, the level of caspase cleaved CK18 is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of caspase cleaved CK18 polypeptide level after 4 hours of EVLP is greater than 80 U/L, 84 U/L, 88 U/L, 92 U/L, 96 U/L or 100 U/L.

In an embodiment, the negative transplant outcome predictor gene product is HMGB-1.

In an embodiment, the test perfusate sample is taken after about 1, 2, 3 or 4 hours of EVLP.

In an embodiment, the level of HMGB-1 polypeptide is increased at least 1.2×, 1.3×, 1.4×, 1.5×, 1.6×, 1.7×, 1.8×, 1.9× or 2× compared to the outcome control.

In an embodiment, the lung graft is identified as a poor candidate for transplant if the level of HMGB-1 polypeptide level after 4 hours of EVLP is greater than 14 ng/mL, 15.6 ng/mL, 20 ng/mL, 25 ng/mL, 30 ng/mL, 35 ng/mL, 40 ng/mL, 50 ng/mL, 60 ng/mL, 70 ng/mL, 80 ng/mL or 90 ng/mL.

In an embodiment, the level of the negative transplant predictor is detected using a ET-1 detection antibody, a big ET-1 detection antibody, a caspase 3 assay, a HMGB-1 detection antibody, M30 kit and/or a M65 kit.

An at least 1.2 fold difference means for example that the level of the biomarker in the test sample is at least 120% the level in an outcome control comparator sample or derived value, for example a good outcome control. Where the outcome control is for example a poor outcome control, a lung graft is a good candidate for transplant if for example the negative transplant predictor gene product is decreased by at least 1.2×, 1.3×, 1.4×, 1.5×, 1.6×, 1.7×, 1.8×, 1.9× or 2× compared to the poor outcome control or for example at least 1.5×, 2×, 3×, 4×, 5×, 6×, 7×, 8×, 9× or 10× compared the poor outcome control.

It is also demonstrated herein that metabolite profiles can be used to classify a DCD lung graft as suitable or not suitable for transplant.

In an embodiment, the metabolite profile comprises for each metabolite of one or more metabolites selected from metabolites listed in FIGS. 14, 15, 16C, 17C, 18A and/or 18C, at least one value corresponding to its level in the test perfusate sample.

In an embodiment, the step of identifying if the lung graft is a good candidate or a poor candidate for transplant comprises using a linear model for microarray data (LIMMA) ANOVA-type classification method. In another embodiment, the identifying if the lung graft is a good candidate or a poor candidate for transplant comprises using a Prediction Analysis of Microarray (PAM) classification method.

In an embodiment, the identifying if the lung graft is a good candidate or a poor candidate for transplant comprises obtaining the metabolite profile of the test sample, the metabolite profile comprising for each metabolite of one or more metabolites, at least one value corresponding to its level in the test sample and comparing the metabolite profile to one or more reference metabolic profiles and identifying the lung graft as a good candidate if the metabolite profile is most similar to a good outcome class reference metabolite profile and identifying the lung graft as a poor candidate if the metabolite profile is most similar to a poor outcome class reference metabolite profile.

In an embodiment, the method involves comparing to a threshold. For example each marker will have a different threshold or cutoff depending on statistical calculations and/or desired test sensitivity and/or specificity. Where more than one metabolite is assessed, a composite score can be determined.

FIG. 14 describes metabolites that were identified as differentially present in 1 hour test perfusate samples from good outcome lungs and poor outcome lungs using LIMMA. In an embodiment the metabolite profile comprises the level of one or more of 5-aminovalerate, taurocholate, glycocholate, betaine, histidine, deoxycarnitine, pyridoxate, urea, propionylcarnitine, and/or pyroglutamine.

FIG. 15 describes metabolites that were identified as differentially present in 4 hour test perfusate samples from good outcome lungs and poor outcome lungs using LIMMA. In an embodiment the metabolite profile comprises the level of one or more of betaine, N-acetylneuraminate, malate, glycocholate, alpha-hydroxyisocaproate, 3-methyl-2-oxobutyrate, taurocholate, 2-methylbutyroylcarnitine, pipecolate, 4-methyl-2, oxopentanoate, methionine, phenylalanine, 5,6-dihydrouracil, pro-hydroxy-pro, histidine, trans-4-hydroxyproline, N1-methylguanosine, valine, trans-urocanate, 2-aminobutyrate, phosphate, lactate, leucine, isoleucine, pyridoxate, isovalerate, 2-octenoyl carnitine, stearidonate (18:4n3), N-acetylmethionine, ribitol, tryptophan, pyroglutamine, tyrosine, hexanoylcarnitine, 5-aminovalerate, pantothenate, 3-hydroxyisobutyrate, tryptophan, betaine, cis-aconitate and proline.

Figure 16:
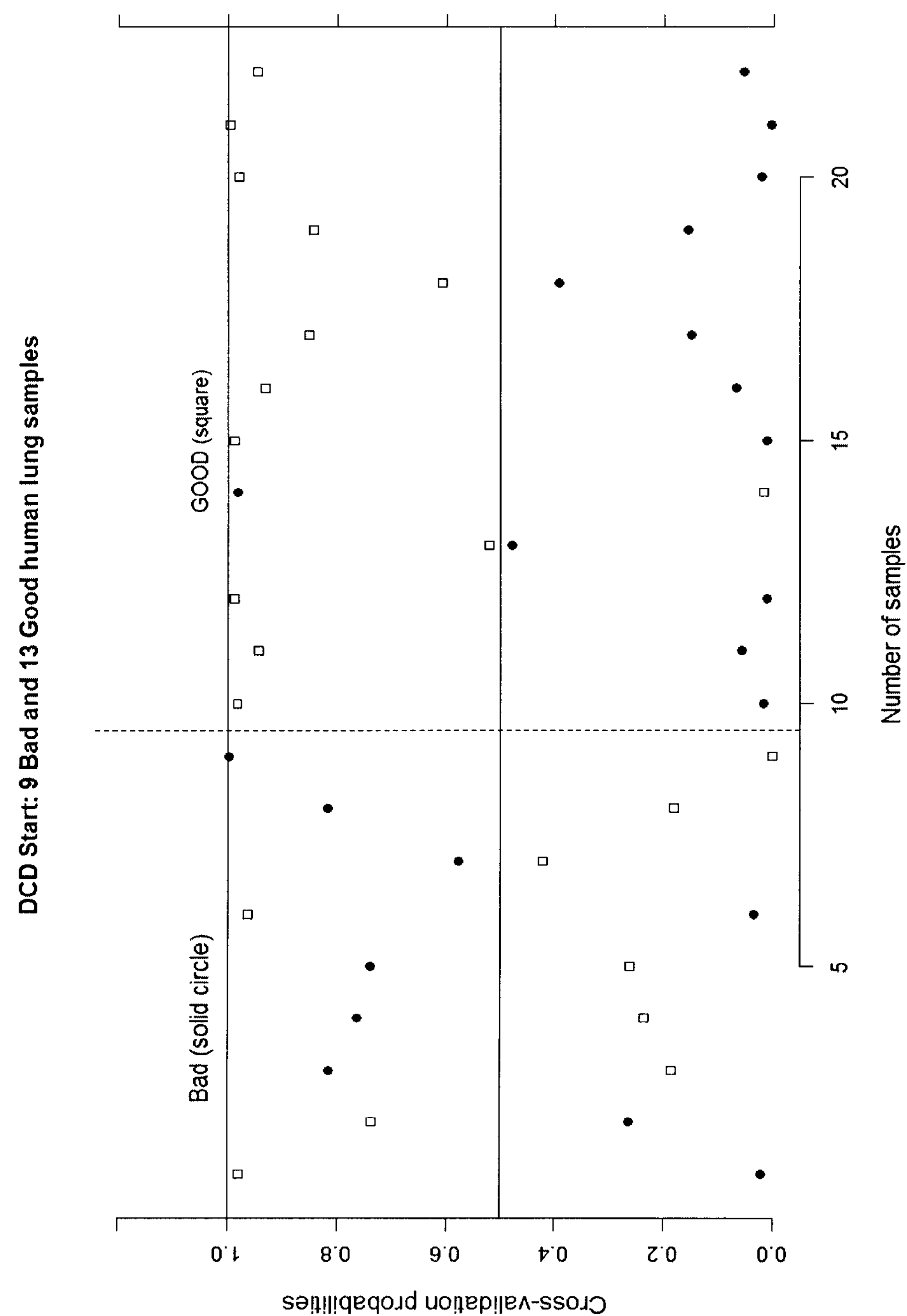
FIG. 16A: Misclassification errors for different number of metabolites—Start EVLP in DCD lung EVLP test perfusate for all (i) or bad and good (ii) lungs.
FIG. 16B: DCD Start EVLP; Cross-validated sample probabilities from the nearest shrunken centroid classifier.
FIG. 16C: describes metabolites that were identified as differentially present in 1 h test perfusate samples from good outcome lungs and poor outcome lungs using a Prediction Analysis of Microarray (PAM) classification method.

FIG. 16C describes metabolites that were identified as differentially present in 1 hour test perfusate samples from good outcome lungs and poor outcome lungs using PAM. In an embodiment the metabolite profile comprises the level of one or more of 5-aminovalerate, serine, taurocholate, glycocholate, mannitol, guanine, glutamate, stearidonate (18:4n3), glycine, histidine, pyridoxate, urea, phosphoethanolamine, ascorbate (Vitamin C), betaine, arginine, aspartate, 3-(4-hydroxyphenyl)lactate, 3-methyl-2-oxobutyrate, guanosine, sorbitol, pro-hydroxy-pro, alpha-hydroxyisocaproate, 2-hydroxybutyrate (AHB), 2-aminobutyrate, 5,6-dihydrouracil, uracil, isobutyrylcarnitine, N-acetylneuraminate, butyrylcarnitine, alanine, pyroglutamine, malate propionylcarnitine, lysine, 2-methylbutyroylcarnitine, deoxycarnitine, pipecolate, alpha-hydroxyisovalerate, asparagine, carnitine, fucose, bilirubin (Z,Z), methionine, 4-methyl-2-oxopentanoate, docosapentaenoate (n6 DPA; 22:5n6), isovalerylcarnitine, trans-4-hydroxyproline, ranitidine, ribose, gamma-glutamylleucine, 1-palmitoylglycerophosphoethanolamine, 3-hydroxyoctanoate, 7-alpha-hydroxy-3-oxo-4-cholestenoate (7-Hoca), cytosine-2',3'-cyclic monophosphate, 3-hydroxybutyrate (BHBA), cis-4-decenoyl carnitine, 3-methyl-2-oxovalerate, pantothenate, N-acetylmethionine, isoleucine, tyrosine, linolenate [alpha or gamma; (18:3n3 or 6)], cysteine, 3-dehydrocarnitine, proline, N-acetylthreonine and/or xylitol.

Figure 17:
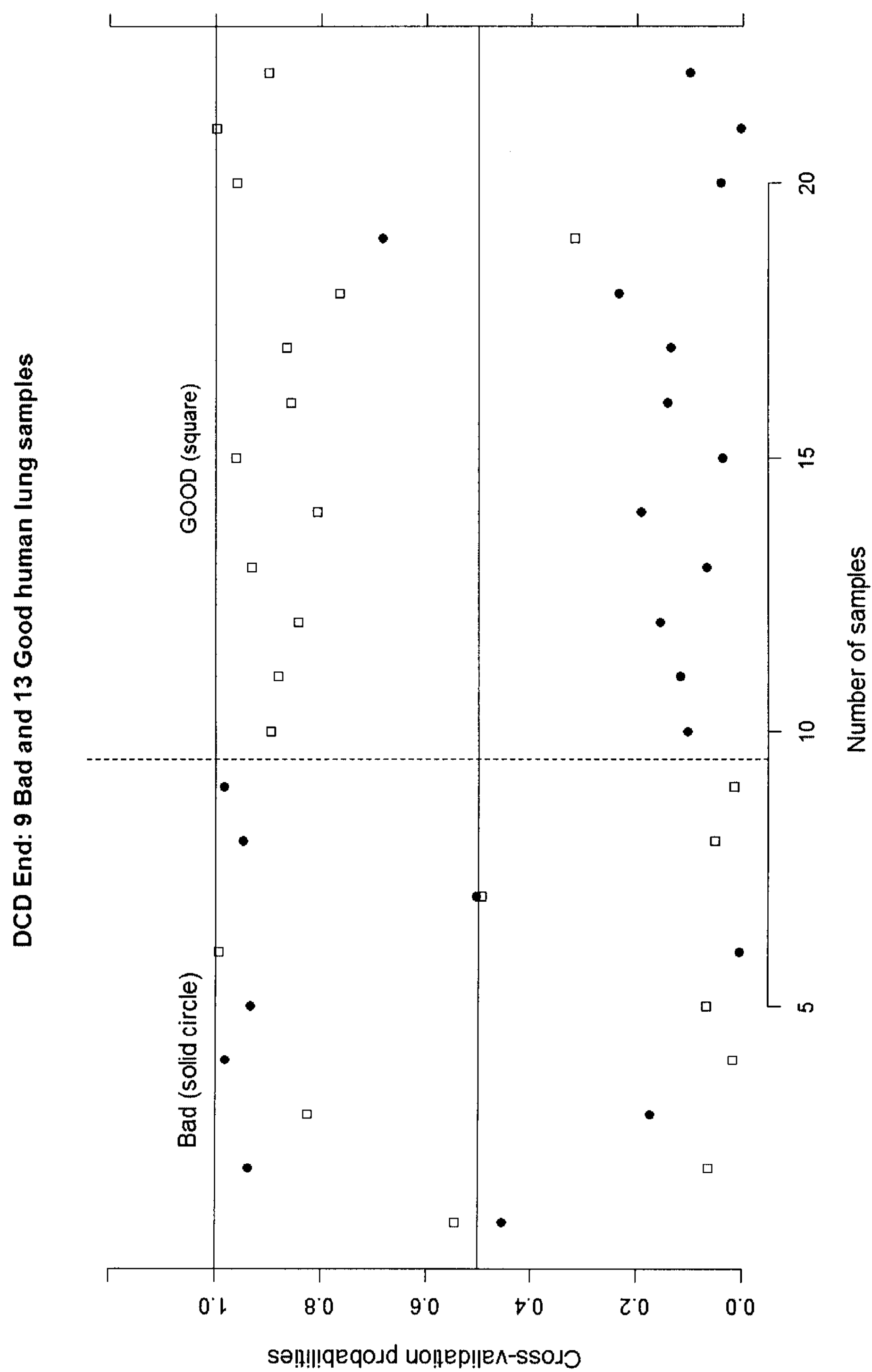
FIG. 17A: Misclassification errors for different number of metabolites—End EVLP in DCD lung EVLP test perfusate for all (i) or bad and good (ii) lungs.
FIG. 17B: DCD End EVLP; Cross-validated sample probabilities from the nearest shrunken centroid classifier.
FIG. 17C: describes metabolites that were identified as differentially present in 4 h test perfusate samples from good outcome lungs and poor outcome lungs using PAM.

FIG. 17C describes metabolites that were identified as differentially present in 4 hour test perfusate samples from good outcome lungs and poor outcome lungs using PAM. lysine, cystine, glycine, 2-aminoadipate, serine, ornithine, arginine, trans-4-hydroxyproline, alanine, fucose, butyrylcarnitine, 3-(4-hydroxyphenyl)lactate, phosphoethanolamine, xylitol, alpha-hydroxyisocaproate and/or N-acetylneuraminate.

FIGS. 16C and 17C also identify in bold metabolites that were identified as differentially expressed in 1 hour and 4 hour test perfusates using LIMMA and PAM. These are listed in FIGS. 18A and 18B.

In an embodiment, the metabolite profile comprises one or more of 5-aminovalerate, taurocholate, glycocholate, histidine and betaine, and/or one or more of 2-aminoadipate, trans-4-hydroxyproline, alanine, fucose, 3-(4-hydroxyphenyl)lactate, xylitol, alpha-hydroxyisocaproate and/or N-acetylneuraminate.

In an embodiment, the metabolite profile comprises one or more of 5-aminovalerate, taurocholate, glycocholate, histidine and/or betaine. In another embodiment, the metabolite profile comprises one or more of 2-aminoadipate, trans-4-hydroxyproline, alanine, fucose, 3-(4-hydroxyphenyl)lactate, xylitol, alpha-hydroxyisocaproate and/or N-acetylneuraminate.

In an embodiment, the one or more of metabolites comprises at least 2, 3, 4 or 5 metabolites.

In an embodiment, the one or more metabolites comprises at least 6, 7, 8, 9 or 10 metabolites.

In an embodiment, the one or more metabolites comprise metabolites with a fold increase of at least 2×.

In an embodiment, the one or more metabolites comprises metabolites in any one of FIG. 14, 15, 16C, 17C, 18A or 18C with a p value of at least 0.05.

The metabolite profile can be determined using a variety of methods known in the art. As demonstrated herein metabolites can be determined using liquid chromatography and/or mass spectrometry methods. In an embodiment, the metabolite profile is determined using liquid chromatography and/mass spectrometry.

In an embodiment, the metabolite profile is determined using ultrahigh performance liquid chromatography/tandem mass spectrometry (UHPLC/MS/MS2) or gas chromatography/mass spectrometry (GC/MS).

In an embodiment, UHPC/MS/MS2 is optimized for basic species or acidic species. This can be accomplished using methods known in the art.

Additional metabolites can also be detected. In an embodiment, the metabolites present in a test sample optionally test perfusate sample are identified by automated comparison of ion features in the experimental samples to a reference library of chemical standard entries that include retention time, molecular (m/Z) preferred adducts, and/or in source fragments and associated MS spectra.

In an embodiment, the test perfusate sample is taken at approximately 1 hour after EVLP and the metabolite profile comprises the level of one or more of the metabolites in FIG. 14 or FIG. 16C.

In an embodiment, the test perfusate sample is taken at approximately 4 hours after EVLP and the metabolite profile comprises the level of one or more of the metabolites in FIG. 15 or 17C.

In an embodiment, the test perfusate sample is taken at approximately 1 hour after EVLP and the metabolite profile comprises the level of one or more of the metabolites in FIG. 18A.

In an embodiment, the test perfusate sample is taken at approximately 4 hours after EVLP and the metabolite profile comprises the level of one or more of the metabolites in FIG. 18B.

Standard curves can also be developed for each metabolite so that test samples, optionally test perfusate samples taken at other times can be used in the present methods.

In an embodiment, the reference metabolic profile comprises a standardized centroid value of the one or more metabolites for each of a good outcome class comprising metabolite levels for a plurality of good outcome lung grafts and a poor outcome class comprising metabolite levels for a plurality of poor outcome lung grafts, wherein the average intensity for each metabolite in each class is divided by the within-class standard deviation for that metabolite to provide a standardized centroid value for the one or more metabolites for each class.

In an embodiment, the comparing the metabolite profile to one or more reference metabolic profiles comprises determining a test sample, optionally test perfusate sample centroid value for the test sample metabolite profile, comparing the test sample centroid value to each of the good outcome and poor outcome centroid values, wherein the class whose centroid value is closest to, in squared distance, to the test sample centroid value is the predicted outcome class for the test sample.

In an embodiment, the good outcome lung grafts are characterized as being suitable for clinical transplantation after EVLP and in the recipient after transplantation, being free from inducing death from graft-related causes within 30 days, PGD or Extra-Corporeal Life Support.

In an embodiment, the poor outcome lung grafts are characterized as being unsuitable for clinical transplantation after EVLP or, in the recipient after transplantation, inducing death from graft-related causes within 30 days, PGD or requiring Extra-Corporeal Life Support.

III. Immunoassays and Kits

In an embodiment the kit comprises an immunoassay for two or more of the negative transplant predictor gene products. In an embodiment, the kit comprises one or more of a 96-well plate, coupled magnetic beads, detection antibodies, standards, assay buffer, wash buffer, sample diluent, standard diluent, detection antibody diluent, streptavidin-PE, a filter plate and sealing tape. In an embodiment the kit comprises detection antibodies or assays for detecting two or more gene products selected from CCG predictor gene products M-CSF, IL-8 SCGF-beta, GRO-alpha, G-CSF, MIP-1 alpha, and/or MIP-1beta, endothelin predictor gene products endothelin 1 (ET-1) and/or big ET-1, and/or apoptosis predictor gene products cytokeratin 18 (CK-18), caspase 3 and/or HMGB-1.

In an embodiment, caspase cleaved CK-18 and/or intact CK-18 is detected.

In an embodiment, the kit further comprises detection agents for other known lung graft outcome markers The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Protein Expression Profiling Predicts Graft Performance in Clinical Ex Vivo Lung Perfusion Objective To study the impact of normothermic ex vivo lung perfusion (EVLP) on cytokines, chemokines and growth factors and their correlation with graft performance either during perfusion or after implantation. Biomarkers discovered in this project will improve diagnostic accuracy during EVLP and also guide treatment strategies.

Methods

High-risk brain death donors and donors after cardiac death underwent 4-6 hours EVLP with intent to transplant. Using a multiplex magnetic bead array assay, multiple analytes were evaluated in perfusate samples. Donor lungs were divided into three groups: I. Control: bilateral transplantation with good early outcome (absence of PGD grade 3, or PGD3); II. PGD3: bilateral lung transplantation with PGD3 anytime within 72 hours; III. Declined: lungs rejected following EVLP. Single-lung transplants and patients bridged to LTx with extracorporeal life support were excluded.

Perfusate samples were collected at 1 hour and 4 hours of EVLP and stored at −80° C. Perfusate levels of 51 analytes (cytokines, chemokines and growth factors) were evaluated in 50 μl samples. Kits (Bio-plex Pro™ Human Cytokine 27-plex Assay and Bio-plex Pro™ Human Cytokine 21-plex Assay, both from Bio-Rad Laboratories, Hercules, Calif.) were used according to manufacturer's instructions and read with Luminex® 100 Analyzer. Data was extracted with Bio-plex Manager™ 6.0 and the concentration of each analyte was given as pg/ml.

Findings

Of 50 cases included in this study, 27 were in group I, 7 in group II and 16 in group III. At 1 hour of EVLP, M-CSF (48.4±12.8 vs. 26.3±2.1 pg/ml, p=0.028) and IL-8 (723.1±543.6 vs. 63.5±11.2 pg/ml, p=0.026) were significantly higher in PGD3 cases compared to controls. For M-CSF, a cut-off of 37 pg/ml rendered a sensitivity of 57.1% and a specificity of 81.4% (AUC=0.77). For IL-8, a cut-off of 84.4 pg/ml had a sensitivity of 71.4% and specificity of 85.1% (AUC=0.77). In the Declined group, SCGF-β (491.4±58.1 vs. 255±19.1 pg/ml, p<0.0001) was significantly higher compared to controls and rendered discrimination with a cut-off at 327 pg/ml, with 81.2% sensitivity and 81.4% specificity (AUC=0.86).

At 4 hours of EVLP, IL-8 (6195±1456 vs. 1746±328.9 pg/ml, p<0.001) and GRO-α (2031±778.8 vs. 519±76.8 pg/ml, p=0.001) were higher in PGD3 group. These two analytes had excellent discrimination with controls, with a cut-off of 3570 pg/ml, IL-8 had a sensitivity of 85.7% and specificity of 92.5% (AUC=0.93), and with a cut-off of 892 pg/ml, GRO-α had a sensitivity of 85.7% and specificity of 85.1% (AUC=0.89). G-CSF (7547±3413 vs. 3338±1122 pg/ml, p=0.008), MIP-1α (88.9±31.2 vs. 18.6±5.4, p=0.009) and MIP-1β (4336±1606 vs. 737.1±21.8 pg/ml, p=0.008) were also significantly higher in PGD3 cases, with a good discrimination with controls.

Conclusion: Perfusate protein expression can differentiate lungs with good outcome from lungs that were declined during EVLP or developed PGD3 after transplantation.

Figure 2:
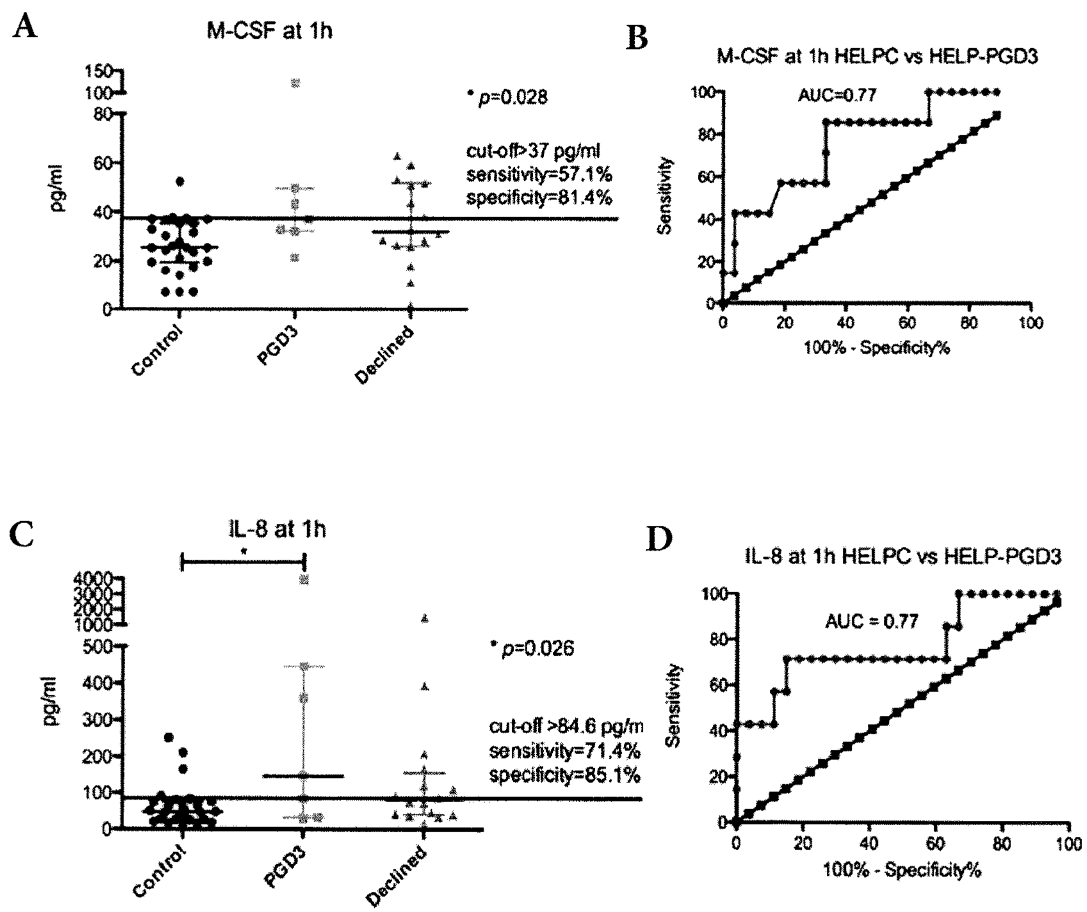
FIG. 2: Is a series of groups showing analyte concentration at 1 hour (FIGS. 2A and 2C) and their respective sensitivity and specificity values (FIGS. 2B and 2D).

FIG. 2 shows that 1 hour analyte is higher in PGD3. At 1 hour of EVLP, M-CSF (48.4±12.8 vs 26.3±2.1 pg/ml, p=0.028) (FIG. 2A) and IL-8 (723.1±543.6 vs. 63.5±11.2 pg/ml, p=0.026) (FIG.2C) were significantly higher in PGD3 cases compared to controls. For M-CSF, a cut-off of 37 pg/ml rendered a sensitivity of 57.1% and a specificity of 81.4% (AUC=0.77) (FIG. 2B). For IL-8, a cut-off of 84.4 pg/ml had a sensitivity of 71.4% and specificity of 85.1% (AUC=0.77) (FIG.2D).

In the Declined group, SCGF-β (491.4±58.1 vs. 255±19.1 pg/ml, p<0.0001) was significantly higher compared to controls and rendered discrimination with a cut-off at 327 pg/ml, with 81.2% sensitivity and 81.4% specificity (AUC=0.86).

Figure 3:
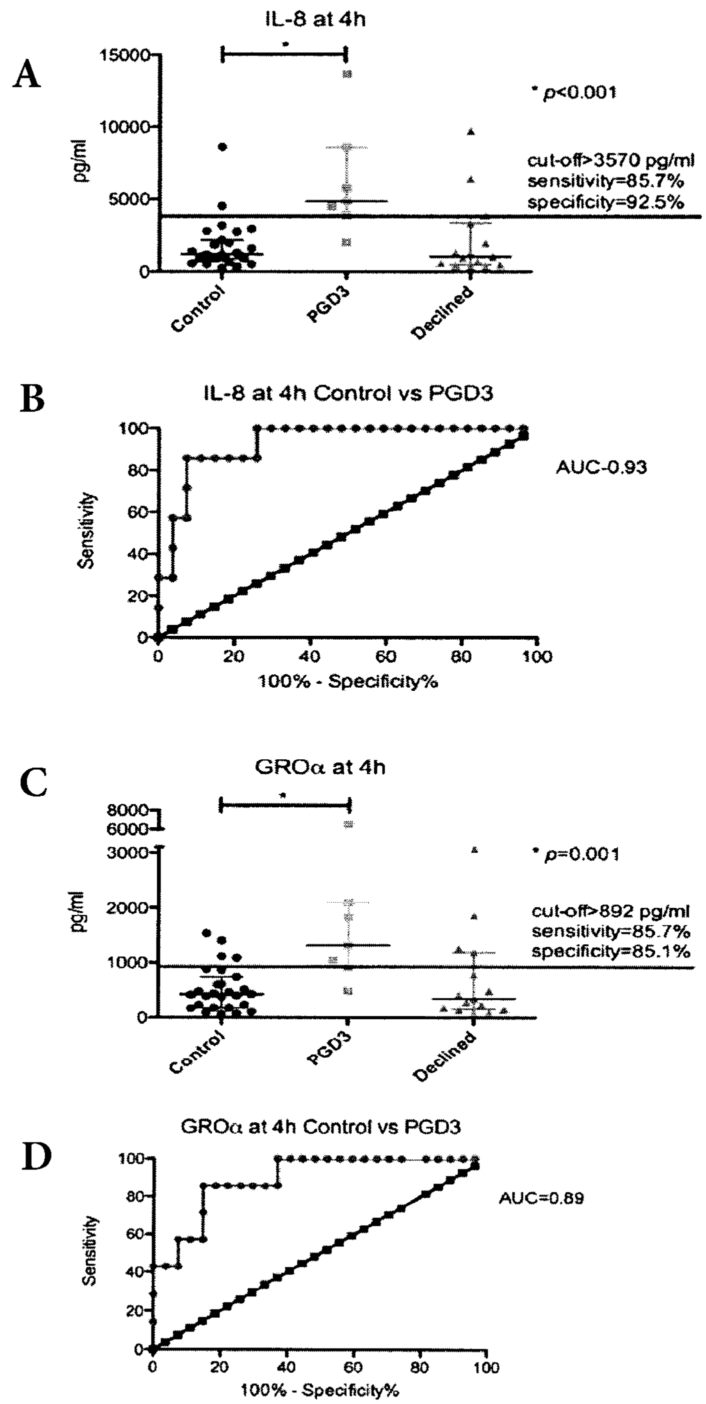
FIG. 3: Is a series of groups showing analyte concentration at 4 hours (FIGS. 3A and 3D) and their respective sensitivity and specificity values (FIGS. 3B and 3D).

FIG. 3 demonstrates that 4 hour analytes are higher in PGD3. At 4 hours of EVLP, IL-8 (6195±1456 vs. 1746±328.9 pg/ml, p<0.001)(FIG.3A) and GRO-α (2031±778.8 vs. 519±76.8 pg/ml, p=0.001) (FIG. 3C) were higher in PGD3 group. These two analytes had excellent discrimination with controls, with a cut-off of 3570 pg/ml, IL-8 had a sensitivity of 85.7% and specificity of 92.5% (AUC=0.93) (FIG. 3B), and with a cut-off of 892 pg/ml, GRO-α had a sensitivity of 85.7% and specificity of 85.1% (AUC=0.89) (FIG. 3D).

G-CSF (7547±3413 vs. 3338±1122 pg/ml, p=0.008), MIP-1α (88.9±31.2 vs. 18.6±5.4, p=0.009) and MIP-1β (4336±1606 vs. 737.1±21.8 pg/ml, p=0.008) were also significantly higher in PGD3 cases, with a good discrimination with controls.

4 Hour Analytes are Higher in Declined

Similar to 1 hour of EVLP, HGF (3642±639.9 vs. 2242±204.1 pg/ml, p=0.038), IL-1ra (180.7±35.8 vs. 115±17.7 pg/ml, p=0.043) and SCGF-β (769.4±133.5 vs. 389.4±32.5 pg/ml, p=0.004) were higher in the Declined cases compared to controls at 4 hours of EVLP. Again, SCGF-β provided reasonable discrimination between groups.

Conclusions

These findings narrow the number of potential biomarkers in EVLP.

Cytokines at 1 h EVLP correlated more with declined lungs, while cytokines at the END correlated more with PGD3 group.

Highlights the role of neutrophils and macrophages in primary graft dysfunction.

Example 2

Endothelin-1 and Big-Endothelin-1 as Potential Biomarkers in Clinical Ex Vivo Lung Perfusion Objective Normothermic ex vivo lung perfusion (EVLP) is a preservation technique that allows reassessment and improvement of donor lungs prior to transplantation. To study the impact of EVLP on Endothelin-1 (ET-1) axis and its correlation with graft performance either during perfusion or after implantation. Biomarkers discovered in this project will improve diagnostic accuracy during EVLP and also guide treatment strategies.

Methods

High-risk DBD and DCD donors underwent 4-6 hours EVLP with intent to transplant. Using a multiplex magnetic bead array assay, levels of ET-1 were assessed, big ET-1 and endothelin converting enzyme 1 (ECE-1) in the perfusates of donor lungs during EVLP. Donor lungs were divided into three groups: I. Control: bilateral transplantation with good early outcome (absence of PGD grade 3 (PGD3)); II. PGD3: bilateral lung transplantation with PGD grade 3 anytime within 72 hours; III. Declined: lungs rejected following EVLP. Single-lung transplants and patients bridged to LTx with extracorporeal life support were excluded.

Perfusate samples were collected at 1 hour and 4 hours of EVLP and stored at −80° C. Perfusate levels of ET-1 axis proteins were measured using ELISA kits for: ET-1 (ET-1 quantikine ELISA kit, R&D systems, Minneapolis, Minn.), big ET-1 (big ET-1 human ELISA kit, Enzo Life Sciences, Farmingdale, N.Y.) and ECE-1 (ECE-1 ELIZA kit, USCN Life Science, Houston, Tex.).

Findings

There were 25 cases in group I, 7 in group II and 16 in group III. At 1 hour of EVLP, perfusates of declined lungs had significantly higher levels of ET-1 (3.1±2.1 vs. 1.8±2.3 pg/ml, p=0.01) and big ET-1 (15.8±14.2 vs 7.0±6.5, p=0.001) compared to control lungs.

At the 4 hours of EVLP, declined lungs also had higher levels of ET-1 (2.7±2.2 vs. 1.3±1.1 pg/ml, p=0.007) and big ET-1 (31.7±17.4 vs 19.4±9.5 pg/ml, p=0.007) compared to controls. In DBD lungs the ET-1 axis did not show significant differences between groups. However for DCD cases, groups II and III had higher ET-1 and big ET-1 levels at the end of perfusion when compared to group I (group II vs. I: ET-1 p=0.03, big ET-1 p=0.01; group III vs. I: ET-1 p=0.007, big ET-1 p=0.003). There were no differences in ECE-1 levels between groups.

Conclusion: In DCD lungs ET-1 and big ET-1 in perfusate predicted outcomes after lung transplantation. They were also associated with non-utilization of lungs after EVLP and thus could represent useful biomarkers to improve selection of donor lungs.

Figure 4:
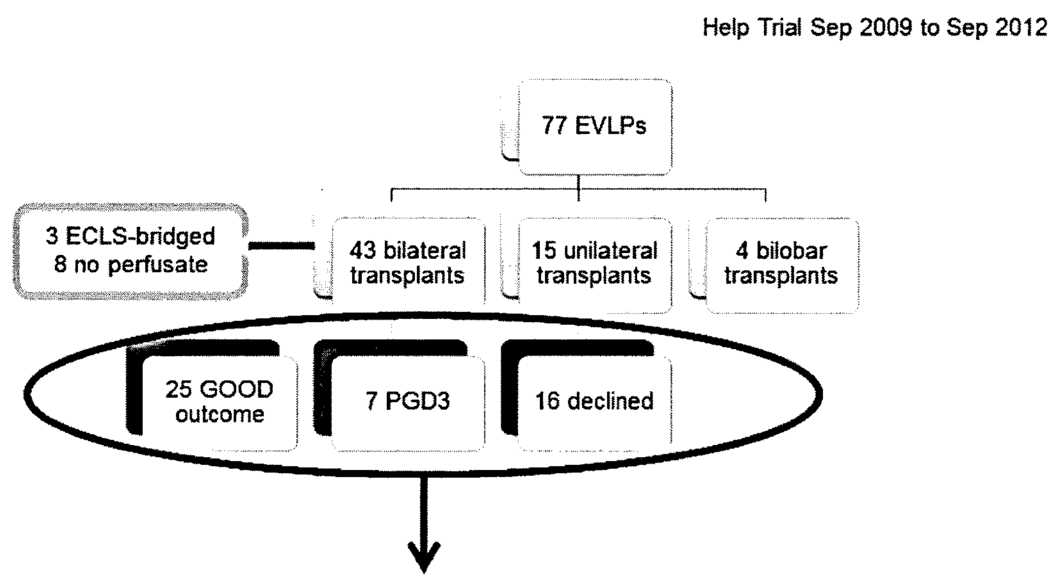
FIG. 4: Shows a schematic of the HELP trial.

FIG. 4 shows study groups: perfusate samples at 1 hour and 4 hours EVLP Analysis by ELISA for ET-1, Big ET-1 and ET-1 Converting Enzyme.

Figure 5:
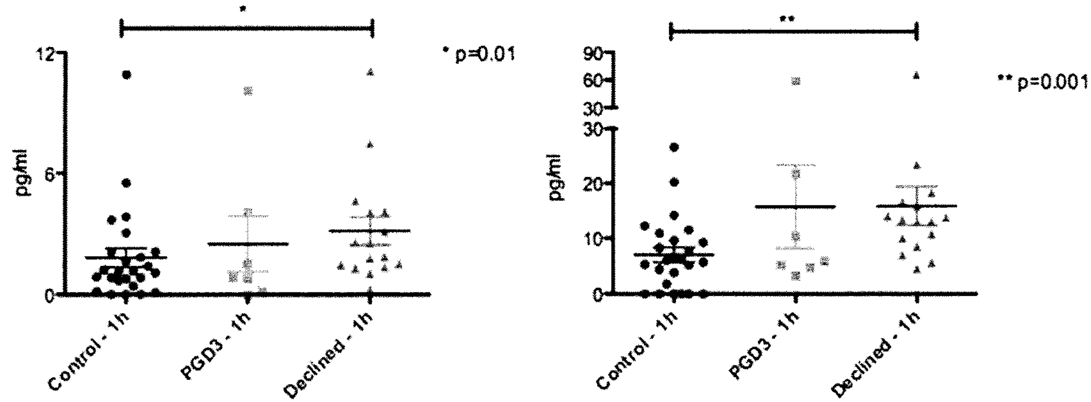
FIG. 5: Is a series of graphics.

FIG. 5 shows at 1 hour of EVLP, perfusates of declined lungs had significantly higher levels of ET-1 (Figure A) (3.1±2.1 vs 1.8±2.3 pg/ml, p=0.01) and big ET-1 (Figure B) (15.8±14.2 vs 7.0±6.5, p=0.001) compared to control lungs.

Figure 6:
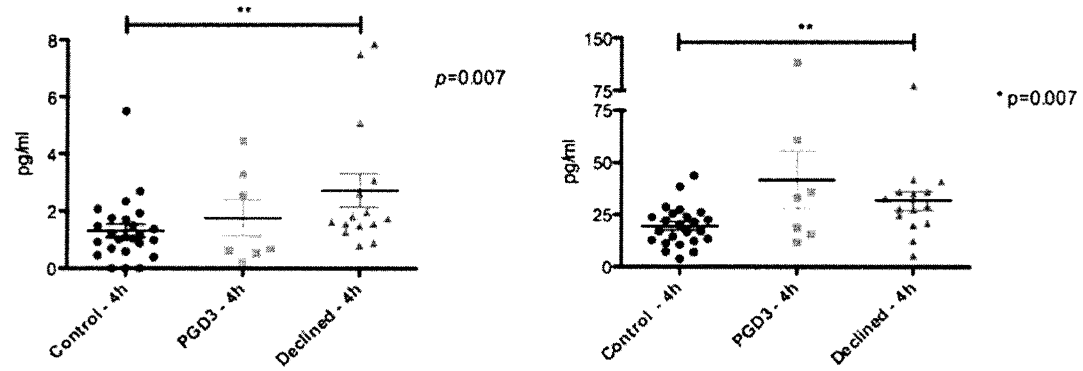
FIG. 6: Is a series of graphics.

FIG. 6 shows at 4 hours of EVLP, declined lungs also had higher levels of ET-1 (Figure A) (2.7±2.2 vs 1.3±1.1 pg/ml, p=0.007) and big ET-1 (Figure B) (31.7±17.4 vs 19.4±9.5 pg/ml, p=0.007) compared to controls.

Figure 7:
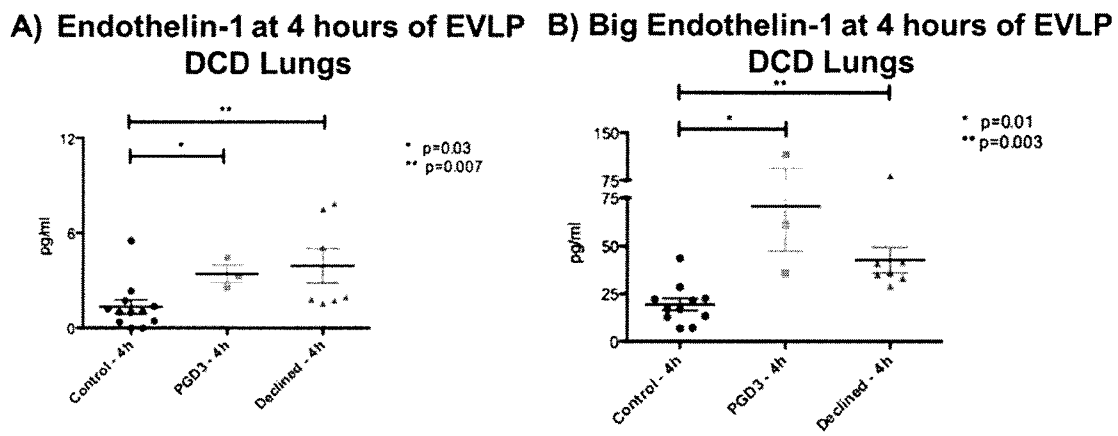
FIG. 7: Is a series of graphics.

For donors after cardiac death, groups II and III had higher ET-1 and big ET-1 levels at the end of perfusion when compared to group I (group II vs I: ET-1 p=0.03, big ET-1 p=0.01; group III vs I: ET-1 p=0.007, big ET-1 p=0.003) (FIG. 7).

Figure 8:
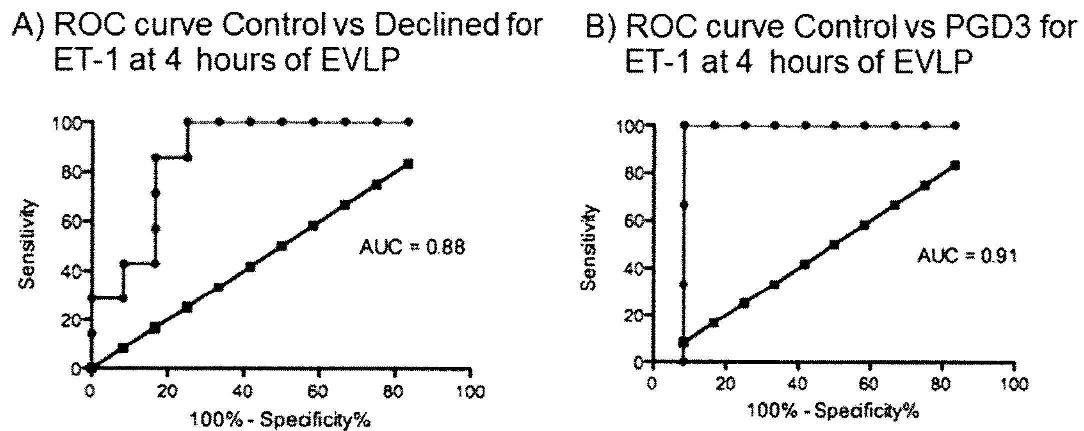
FIG. 8: Is a series of groups showing Receiver Operating Characteristic (ROC) curve control vs. declined for ET-1 at 4 hours of EVLP.

In FIG. 8A ET-1 has an accuracy of 88% to detect Declined lungs from donors after cardiac death. In FIG. 8B. Accuracy of ET-1 to detect PGD3 lungs from donors after cardiac death is 91%.

In FIG. 9A, Big ET-1 has an accuracy of 92% to detect Declined lungs from donors after cardiac death. In FIG. 9B, accuracy of Big ET-1 to detect PGD3 lungs from donors after cardiac death is 96%.

Conclusions

ET-1 axis is involved in EVLP.

ET-1 and Big ET-1 are increased in lungs declined after EVLP (1 h and 4 hs).

The relevance of ET-1 and Big ET-1 as potential biomarkers is increased in DCD cases, when there is also association with PGD3 cases.

Example 3

Title: Apoptosis, not Necrosis, During Ex-Vivo Lung Perfusion is Correlated with Severe PGD Body 1: It was hypothesized that a donor lung which develops more apoptosis during ex-vivo lung perfusion (EVLP) tends to experience severer primary graft dysfunction (PGD) after transplant and that cell death markers in perfusate can be used for prediction of subsequent PGD3.

Body 2: This is a single-institution retrospective case-control study. A correlation of the outcome of recipients after EVLP and cell death markers in EVLP perfusate was investigated. From 2008 to 2012, 77 high-risk donor lungs were subjected to normothermic acellular EVLP for 4 to 6 hours. Lungs were judged for transplantation based on physiological assessment. The cases (PGD group, N=8) were patients who developed PGD 3 within 72 h after lung transplant. The matched controls (Control group, N=8) were selected from patients who had PGD 0, 1 or 2 within 72 h after transplant. Matching factors were recipient age, gender and lung disease. A matched design was used to minimize biases of recipient factors affecting the outcome. Cell death markers including M30, M65 and HMGB-1 were measured with ELISA in perfusate at 1 h and the end of EVLP.

Body 3: M30 which indicates epithelial apoptosis did not show a significant difference between two groups in perfusate at 1 h. However, M30 in PGD group was significantly higher compared to Control group at the end of EVLP (p=0.015). M30 at the end of EVLP increased significantly compared to 1 h (p=0.016). M65 which indicates epithelial apoptosis and necrosis did not show a significant difference between two groups in both time-points. HMGB-1, which is a mediator of inflammation/immune response and released from dead cells, was significantly higher in PGD group at the end (p=0.035) but not at 1 h of EVLP. Using ROC curve, AUC of M30 at the end of EVLP was 0.84 (95% Cl: 0.62-1.06, p=0.035) and AUC of HMGB-1 at the end of EVLP was 0.85 (95% Cl: 0.64-1.06, p=0.029).

Body 4: Epithelial cell apoptosis is related to subsequent PGD3, but necrosis did not correlate with PGD severity. M30 and HMGB-1 are predictive perfusate markers for PGD3.

Hypothesis and Objectives

Hypothesis: Based on background, it was hypothesized: A lung which develops more apoptosis during EVLP tends to experience more PGD after transplantation. And, cell death markers in perfusate can be used for prediction of subsequent PGD.

Objectives: To prove this hypothesis, a correlation of the outcome of consecutive recipients undergoing transplantation after EVLP for high-risk donor lungs and findings relevant to cell death pathway were studied. The Specific Aims of this study were: 1) To investigate the significance of cell death pathway as a trigger for deterioration during EVLP and PGD. 2) To develop perfusate markers related to cell death/injury for severe PGD.

Methods

Study Design: This is a single-institution retrospective case-control study using collected material and clinical data in lung transplantation using EVLP. A correlation of the outcome of recipients after EVLP for high-risk donor lung and cell death pathway in the lung was investigated. From September 2008 to September 2012, 77 high-risk donor lungs were subjected to normothermic acellular EVLP for 4 hours with hourly functional assessments. High-risk donor lungs were defined as those that had any of the following: (A) best P/F less than 300 mm Hg; (B) pulmonary edema detected on the last chest x-ray; (C) poor lung compliance during examination of the lungs during donor operation; (D) donation after cardiac death; and (E) high-risk history, such as multiple (>10 units) blood transfusions or history of aspiration. Donor lungs with established pneumonias, gross contusions in more than 1 lobe, and evidence of aspiration of gastric contents were excluded.

Figure 10:
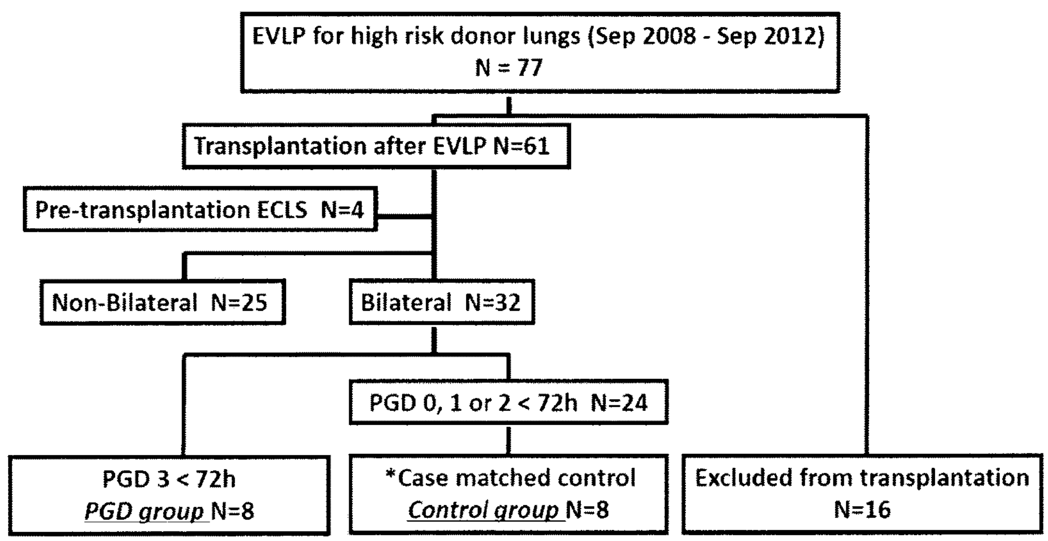
FIG. 10A: Patient selection process. Matched factors for the final sample selection included: recipient age (±10 years), recipient gender, recipient lung disease. PGD=primary graft dysfunction. EVLP=ex-vivo lung perfusion; ECLS=extra corporeal life support.
FIG. 10B: Is a sample collection schematic.
FIG. 10C: M30 and M65: Cell death makers.
FIG. 10D: Demonstrates the Structure of Cytokeratin18.
Figure 10:
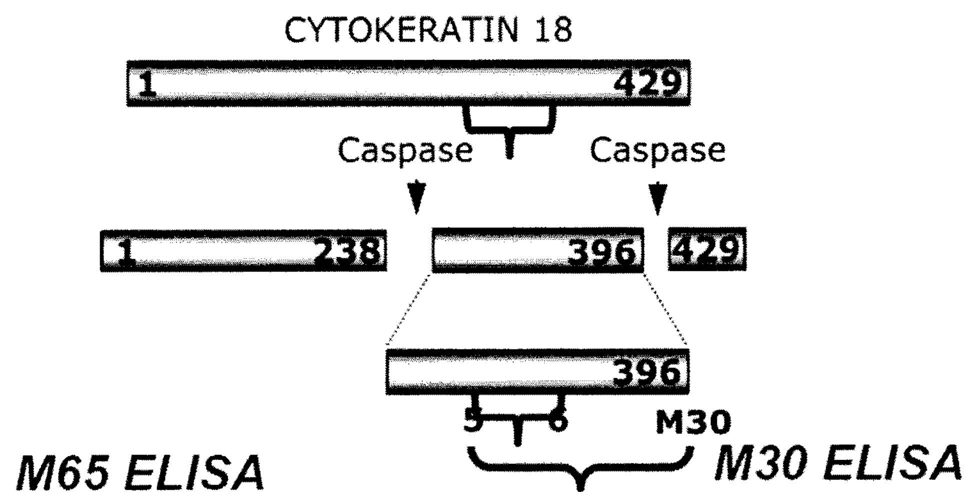

The case selection process is shown in FIG. 10A. Lungs which were considered as risky according to the assessment with EVLP were rejected from transplantation (Rejected lung group N=16). The recipients who were treated with extracorporeal life support before transplantation and who received single or lobe lung transplantation were excluded from this analysis. The cases (PGD group N=8) are patients who developed PGD3 within 72 hours after transplant (The International Society for Heart and Lung Transplantation Grading System for PGD) (11). The matched controls (Control group N=8) are selected from patients who had PGD 0, 1 or 2 within 72 hours after transplant. A matched design was used to minimize biases that might arise from other factors affecting the recipient outcome. Matched factors were recipient age (±10 years), recipient gender and recipient lung disease. Recipients provided written informed consent to participate in this study in accord with the protocol, which was approved by the University Health Network Research Ethics Board.

Technique and assessment in ex-vivo lung perfusion: The detailed acellular EVLP technique has been described (5). In brief, donor lungs were retrieved in a standard fashion, transported from the donor hospital to the center under standard conditions of cold storage in a low potassium dextran solution (Perfadex®, Vitrolife), and placed in the EVLP circuit. The circuit was primed with 2 litres of Steen Solution™ (XVIVO, Vitrolife). This solution is a buffered dextran containing an extracellular-type solution with an optimized colloid osmotic pressure developed specifically for EVLP. Additionally, 500 mg of methylprednisolone (Solu-Medrol®; Sandoz Canada, Boucherville, Canada), 500 mg of imipenem/cilastatin (Primaxin®; Merck, Whitehouse Station, N.J.), and 3000 IU of heparin (Organon, Canada) were added to the perfusate. After the first hour of EVLP, 500 mL of circulated perfusate was removed and replenished with 500 mL of fresh solution. Subsequently, 250 mL was exchanged every hour until the end of EVLP. No blood products were added to the circuit.

The organs were then perfused for 4 hours with hourly functional assessments. Lungs with a $PaO_2/FIO_2$ (P/F) of 400 mm Hg or greater and stable or improving pulmonary artery pressure, airway pressures, or dynamic compliance were considered transplantable. Lungs were excluded for transplantation if the P/F were less than 400 mm Hg or they demonstrated greater than 15% deterioration in the other functional parameters.

Measurement of cell death markers in perfusate: Perfusate was obtained at 1 hour, before designated exchange of solution as noted earlier, and 4 hours of EVLP. Specimens were immediately snap-frozen and stored in −80 degree C. M30 Apoptosense® ELISA, M65 EpiDeath® ELISA (PREVIVA AB, Sweden) and HMGB-1 (High Mobility Group Box1 Protein) ELISA (IBL International, Germany) were used for the perfusate. These three biomarkers detect proteins which are involved in cell death pathway in the lungs. M30 measures caspase-cleaved CK18 produced during apoptosis of epithelial cell and M65 measures the levels of both caspase-cleaved and intact CK18, the latter of which is released from epithelial cells undergoing necrosis. The combination of these two ELISA therefore facilitates the determination of cell death mode and the quantification of dead cells in serum (12). HMGB-1 is a mediator of inflammation/immune response (13, 14) and released from dead cells and considered to be associated with lung injury (15-17).

Statistical analysis: Statistics were calculated with GraphPad Prism® 5 (GraphPad Software Inc., La Jolla, Calif.). Non-parametric Wilcoxon's test was used for comparison of cell death markers level and comparison of short-term outcome of recipient. Student's t-test was used for comparison of characteristics of recipient. Wilcoxon signed-rank test was used to test the change of values of markers from 1 hour to 4 hours of EVLP. In order to evaluate the importance of M30 and HMGB-1 levels for PGD, a receiver operating characteristics (ROC) analysis was performed. All p values were two-sided in tests and p values less than or equal to 0.05 were considered to be statistically significant.

Results

Patient characteristics and post-operative outcomes: Table 1 shows summary of the post-operative outcomes of PGD group

TABLE 1

List of the patients of PGD group. Case 2 died of sepsis in 7 post-operative day. Case 5 was the patient with the most sustained PGD 3. This patient was extubated on 25 days, left from ICU on 30 days and discharged on 120 days after transplantation. Each length in this patient was the longest among PGD group.

| | | | PGD grade | | | |
|---|---|---|---|---|---|---|
| Case | Age/Sex | Diagnosis | ICU | 24 h | 48 h | 72 h |
| 1 | 68/F | Emphysema | 3 | 1 | 2 | 1 |
| 2 | 58/F | Pulmonary fibrosis | 3 | 1 | 1 | 2 |
| 3 | 31/F | Cystic Fibrosis | 3 | 2 | 1 | 1 |
| 4 | 38/F | Pulmonary fibrosis/PAH | 3 | 3 | 3 | 2 |
| 5 | 46/F | Emphysema | 3 | 3 | 3 | 3 |
| 6 | 61/M | Pulmonary fibrosis | 3 | 1 | 2 | 1 |
| 7 | 56/M | Pulmonary fibrosis | 3 | 2 | 3 | 1 |
| 8 | 58/F | Pulmonary fibrosis | 3 | 1 | 2 | 1 |

PGD = primary graft dysfunction; PAH = pulmonary arterial hypertension; ICU = intensive care unit.

TABLE 2

Characteristics of recipients. Age, gender and primary diagnosis of recipient were matched in the PGD group and the Control group. There was no significant difference in recipient characteristics (t-test). In the Control group, six patients had PGD 2 and two patients had PGD 1 at the worst grade within 72 hours aftertransplant. PGD = primary graft dysfunction.

| Characteristics | PGD group n = 8 | Control group n = 8 | p-value |
|---|---|---|---|
| Age (Years) | 52.0 ± 12.5 | 54.0 ± 12.4 | 0.875 |
| Male:Female | 2:6 | 2:6 | — |
| Diagnosis | | | — |
| Pulmonary fibrosis | 5 (62.5%) | 5 (62.5%) | |
| Emphysema | 2 (25.0%) | 2 (25.0%) | |
| Cystic fibrosis | 1 (12.5%) | 1 (12.5%) | |
| Worst PGD grade | | | — |
| PGD 3 | 8 | 0 | |
| PGD 2 | 0 | 6 | |
| PGD 1 | 0 | 2 | |
| | | | t-test |

TABLE 3

Comparison of short-term outcome of recipient. Variables are expressed as mean and interquartile range. Mann-Whitney'stest was used for comparison.

| Clinical outcome | PGD group n = 8 | Control group n = 8 | p-value |
|---|---|---|---|
| Extubation (days) | 4.5 (3, 16) | 2 (1.25, 2.75) | 0.019* |
| Hospital stay (days) | 19.5 (16, 32.5) | 16.5 (14.5, 19) | 0.31 |
| ICU stay (days) | 6 (4.25, 17) | 3 (2.25, 6.25) | 0.10 |

Figure 11:
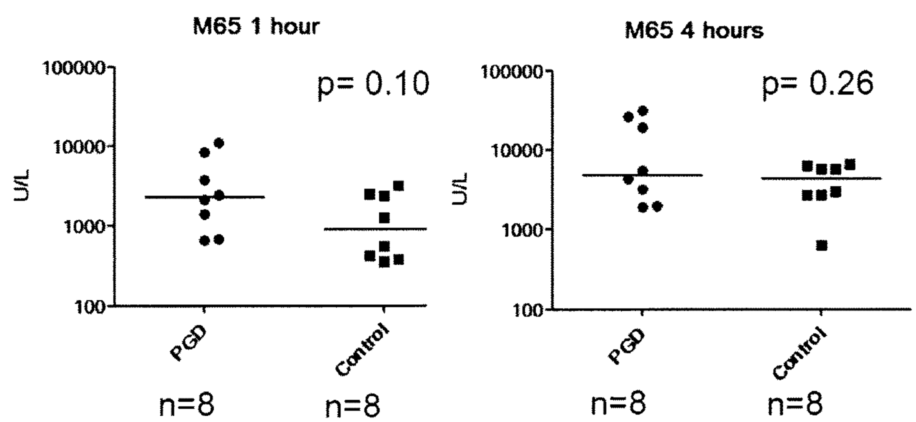
FIG. 11A: Is a Mann Whitney test illustrating that M30 is not significantly different between PGD and control groups at 1 h EVLP. M30 in the PGD group is significantly higher compared to the control group at the end of EVLP at 4 h (p=0.015).
FIG. 11B: Is a Wilcoxon signed-rank test illustrating that M30 in the PGD group increased significantly at the end of EVLP after 4 h compared to 1 h (p=0.016). There is no significant difference in M30 in the control group after 1 h or 4 h EVLP.
FIG. 11C: Is a Mann Whitney test illustrating that M65, which indicates epithelial apoptosis and necrosis, did not show a significant difference between PGD and control groups after 1 h and 4 h EVLP.

Epithelial cell apoptosis, rather than necrosis, in the donor lung during EVLP is related to subsequent PGD 3: M30 did not show a significant difference between two groups in perfusate at 1 hour. However, M30 in PGD group was significantly higher compared to the Control group at 4 hours of EVLP (p=0.015) (FIG. 11). M30 at the 4 hours of EVLP increased significantly compared to 1 hour in the PGD group (p=0.016), but not in the Control group (p=0.078). M65 did not show a significant difference between two groups at both time-points. HMGB-1 was significantly higher in PGD group at 4 hours (p=0.028) (FIG. 12) but not at 1 hour of EVLP. HMGB-1 at the 4 hours of EVLP increased significantly compared to 1 hour in the PGD group (p=0.016), but not in the Control group (p=0.20).

M30 and HMGB-1 are markers for PGD 3: Using ROC curve, AUC of M30 at 4 hours of EVLP was 0.83 (95% Cl: 0.63-1.031, p=0.027) and AUC of HMGB-1 at 4 hours of EVLP was 0.85 (95% Cl: 0.65-1.05, p=0.024) (FIG. 13). If the cut-point of M30 at 4 hours EVLP is set as 92.2 U/L, sensitivity is 50% and specificity is 100%. If the cut-point of HMGB-1 at 4 hours EVLP is set as 15.6 ng/mL, sensitivity is 100% and specificity is 50%.

High value of M30 and HMGB-1 reflect severe post-transplant Outcome: The patient with the highest M30 value (545 U/L) at 4 hours of EVLP, which is indicated as an open circle in FIG. 11, was the only mortality case in PGD group (Case 2). The patient with the highest HMGB-1 value (121 ng/ml) at 4 hours of EVLP, which is indicated as an open circle in FIG. 12, was the most sustained PGD: i.e. only one case of PGD 3 at 72 hours (Case 5).

Conclusion

Epithelial cell apoptosis, rather than necrosis, during EVLP is related to subsequent PGD3.

M30 and HMGB-1 in perfusate could be a "predictive" PGD marker at 4 hours of EVLP.

Highly elevated value of these markers might reflect severe outcome of the recipient.

Example 4

Introduction

In 2011, the early results of a non-randomised clinical trial using acellular normothermic ex vivo lung perfusion (EVLP) for the assessment of 'marginal' donor lungs which normally would have been declined for lung transplantation using conventional criteria for organ selection were reported. In this study, marginal lungs were evaluated with EVLP using physiological parameters to objectively assess the quality of a donor lung. Importantly, 87% of these marginal lungs were deemed to be usable following EVLP assessment, and following lung transplantation, it was found that the early outcome of the recipients of these marginal lungs, including Primary Graft Dysfunction (PGD) incidence, were comparable to a control group of recipients who received donor lungs deemed to be satisfactory by conventional organ selection criteria, and no severe adverse events were directly attributable to EVLP. It was believed that for these marginal donor lungs that underwent EVLP, there is a trend towards a better clinical outcome than the control group, although this did not reach statistical significance.

One of the most significant events that takes place as a donor lung undergoes normothermic EVLP is the transition from the state of cold preservation at four degrees Celsius in Perfadex® solution, the standard practice of lung preservation after organ harvest, to perfusion with Steen Solution™ at 37 degrees Celsius. This change is almost certainly associated with profound alterations in the metabolism in the donor lung. By investigating the metabolic changes in these marginal lungs during EVLP, and understanding the impact of EVLP on these lungs, it may be possible to stratify these donor lungs by their quality, as well as to design repair strategies to salvage injured organs. Metabolomics, the non-biased quantification and identification of all metabolites in a biological system, is based on the premise that changes in the genome, transcriptome or proteome, are reflected as alterations in the metabolite concentrations in biological fluids and tissues. Moreover, the response of metabolism to a perturbation to a biologic system takes as little a few seconds or minutes, whereas it may take several hours to be reflected at the genome level, for example. During EVLP, the harvested lungs are being perfused in isolation with Steen Solution™, and untargeted metabolic profiling of the EVLP perfusion fluid represents a novel window into the biologic changes occurring in these lungs over time during EVLP.

Objectives

Investigation of EVLP using untargeted metabolic profiling of the EVLP perfusion fluid was aimed. Metabolic profiles of the EVLP perfusion fluid from the following groups will be compared: [1] lungs that were Declined after EVLP assessment, and lungs that were transplanted after EVLP but developed Primary Graft Dysfunction (PGD), and [2] lungs that were transplanted after EVLP and did not develop PGD.

Methods

Following the previous report of the HELP study published in the New England Journal of Medicine (24), EVLP for the evaluation of clinically marginal donor lungs was continued to use. The setup of EVLP, inclusion and exclusion criteria for assigning a particular donor lung to EVLP assessment, and the physiological parameters for the determination of the suitability for lung transplantation, have been previously described. Between December 2008 and December 2011, 50 marginal donor lungs were evaluated using EVLP, and seven lungs were deemed unsuitable for transplantation after assessment. The remaining 43 lungs were used for clinical transplantation.

During each EVLP assessment, the EVLP circuit is primed with 2000 ml of Steen Solution™. Subsequently, the circulating Steen Solution™ within the EVLP circuit is replenished in the following manner: at the end of the first hour, one litre of the perfusate is removed from the circuit, and one litre of fresh Steen Solution™ is replaced into the circuit. After this, at the end of each subsequent hour, 500 mL of perfusate fluid is removed from the circuit, and 500 mL of fresh Steen Solution™ is added to the circuit. At the end of the first hour of perfusion and at the end of four hours of perfusion, 10 mL aliquots of the perfusate fluid were withdrawn from the perfusion circuit just before the replacement of perfusion fluid described above, and immediately frozen by placing the container in liquid nitrogen and subsequently stored at −80 degrees Celsius. The paired perfusates from the start and end of EVLP were collected for 50 marginal donor lungs, which included those from seven lungs that were declined for transplantation following EVLP assessment. "Start" samples are taken after 1 hour of perfusion and "end" samples are taken after 4 hours of perfusion. Start and end samples in each of the examples described refer to 1 hour and 4 hour perfusate samples respectfully.

The 50 donor lungs comprise of 28 cases of DBD, and 22 cases of DCD. As stated above, after EVLP assessment, seven out of the 50 lungs were deemed unsuitable by physiological parameters and were declined for transplantation (DT group). Of the remaining forty-three transplanted lungs, PGD3 developed in nine recipients on admission to intensive care unit (PGD group), one of whom required de novo Extracorporeal Membrane Oxygenation (ECMO) support post-transplant. There was one death within 30 days of the transplant which was directly related to the quality of the donor lung, out of the 43 lung transplant recipients. For the purpose of outcome analysis, all donor lungs were designated as 'Good Lungs' if they were deemed usable for clinical transplantation following EVLP assessment, and where the recipients did not develop PGD3 or death within 30 days from graft-related causes. Donor lungs were designated as 'Bad Lungs' if the lungs were deemed unsuitable for clinical transplantation following EVLP, or lungs that were transplanted following EVLP but the recipient developed PGD3 or died from graft-related causes within 30 days.

Sample Preparation and Metabolic Profiling

The non-targeted metabolic profiling instrumentation employed for this analysis combined three independent platforms: ultrahigh performance liquid chromatography/tandem mass spectrometry (UHPLC/MS/MS$^2$) optimized for basic species, UHPLC/MS/MS$^2$ optimized for acidic species, and gas chromatography/mass spectrometry (GC/MS). For each sample, 100 μL was used for analyses. Using an automated liquid handler (Hamilton LabStar, Salt Lake City, UT), protein was precipitated from the plasma or tissue homogenate with methanol that contained four standards to report on extraction efficiency. The resulting supernatant was split into equal aliquots for analysis on the three platforms. Aliquots, dried under nitrogen and vacuum-desiccated, were subsequently either reconstituted in 50 μL 0.1% formic acid in water (acidic conditions) or in 50 μL 6.5 mM ammonium bicarbonate in water, pH 8 (basic conditions) for the two UHPLC/MS/$MS^2$ analyses or derivatized to a final volume of 50 μL for GC/MS analysis using equal parts bistrimethyl-silyl-trifluoroacetamide and solvent mixture acetonitrile:dichloromethane:cyclohexane (5:4:1) with 5% triethylamine at 60° C. for one hour. In addition, three types of controls were analyzed in concert with the experimental samples: aliquots of a well-characterized human plasma pool served as technical replicates throughout the data set, extracted water samples served as process blanks, and a cocktail of standards spiked into every analyzed sample allowed instrument performance monitoring. Experimental samples and controls were randomized across platform run days.

For UHLC/MS/$MS^2$ analysis, aliquots were separated using a Waters Acquity UPLC® (Waters, Millford, Mass.) and analyzed using an LTQ™ MS (Thermo Fisher Scientific, Inc., Waltham, Mass.) which consisted of an electrospray ionization (ESI) source and linear ion-trap (LIT) mass analyzer. The MS instrument scanned 99-1000 m/z and alternated between MS and $MS^2$ scans using dynamic exclusion with approximately 6 scans per second. Derivatized samples for GC/MS were separated on a 5% phenyldimethyl silicone column with helium as the carrier gas and a temperature ramp from 60° C. to 340° C. and then analyzed on a Thermo-Finnigan Trace DSQ™ MS (Thermo Fisher Scientific, Inc.) operated at unit mass resolving power with electron impact ionization and a 50-750 atomic mass unit scan range.

Metabolites were identified by automated comparison of the ion features in the experimental samples to a reference library of chemical standard entries that included retention time, molecular weight (m/z), preferred adducts, and in-source fragments as well as associated MS spectra, and were curated by visual inspection for quality control using software developed at Metabolon (3).

Statistical Analysis

Data Normalization

For studies spanning multiple days, a data normalization step was performed to correct variation resulting from instrument inter-day tuning differences. Essentially, each compound was corrected in run-day blocks by registering the medians to equal one (1.00) and normalizing each data point proportionately (termed the "block correction"). For studies that did not require more than one day of analysis, no normalization is necessary, other than for purposes of data visualization.

The Identification of Differentially Expressed Targets

This is done using LIMMA (linear models for microarray data) to identify differentially expressed targets (25). Briefly speaking, it starts by fitting a linear model for each target in the data, then an empirical Bayes (EB) method is used to moderate the standard errors for each target, which shrinks the standard errors towards a common value. The corresponding p-values for each contrast (differential analysis) were adjusted using the multiple testing procedure developed by Benjamini and Hochberg (26). For the repeated measurements of each subject, subject as a random effect and each subject as a block corresponding to a paired sample were treated. The correlation within block/subject was estimated. The analysis is analogous to mixed model analysis of variance except that information has been borrowed between targets. Information is borrowed by constraining the within-block correlations to be equal between targets and by using empirical Bayes methods to moderate the standard deviations between targets. The adjusted p value of <0.05 is set as significant, which corresponds to a False Discovery Rate of 0.05.

Classification of 'Good Lungs' vs. 'Bad Lungs' based on the metabolic profile of a given EVLP perfusate sample is performed using the Prediction Analysis of Microarray (PAM) algorithm to build the nearest centroid-based classifiers (27). Briefly, the method computes a standardized centroid for each class. This is the average intensity for each molecule in each class divided by the within-class standard deviation for that molecule. Nearest centroid classification takes the intensity profile of a new sample, and compares it to each of these class centroids. The class whose centroid that it is closest to, in squared distance, is the predicted class for that new sample.

To decide the shrinkage threshold, 10-fold cross-validation for a range of threshold values was performed. The samples are divided up at random into 10 roughly equally sized parts. For each part in turn, the classifier is built on the other 9 parts then tested on the remaining part. This is done for a range of threshold values, and the cross-validated misclassification error rate is reported for each threshold value. The threshold value giving the minimum cross-validated misclassification error rate or a balance of error rate and no. of molecules used was chosen.

Lungs were defined as 'Good Lungs' if:

after EVLP the lung was deemed suitable for clinical transplantation, and the outcome was free from death from graft-related causes within 30 days, Primary Graft Dysfunction or Extra-Corporeal Life Support after transplantation.

Lungs were defined as 'Bad Lungs' if:

the lung was deemed unsuitable for clinical transplantation after EVLP evaluation, OR after clinical transplantation the recipient died within 30 days from graft-related causes, developed PGD, or required ECLS.

Results

Untargeted metabolic profiling of the 100 samples of EVLP perfusion fluid detected 312 named biochemicals.

The following differential analysis using LIMMA were performed:

1. differential of DBD lungs at 1 hour EVLP between bad and good lungs
2. differential of DCD lungs at 1 hour EVLP between bad and good lungs
3. differential of DBD lungs at 4 hour EVLP between bad and good lungs
4. differential of DCD lungs at 4 hour EVLP between bad and good lungs Statistical Method 1: Identification of Differentially Expressed Targets LIMMA (Linear Models For Microarray Data)

Starts by fitting a linear model for each target in the data.

An empirical Bayes (EB) method is used to moderate the standard errors for each target, which shrinks the standard errors towards a common value.

The corresponding p-values for each contrast (differential analysis) were adjusted using the multiple testing procedure developed by Benjamini and Hochberg (26).

DBD Bad vs. Good

For DBD lungs, at both 'Start EVLP' and 'End EVLP', using Adjusted p values of <0.05 or 0.1, there were no metabolites that could differentiate 'Bad Lungs' from 'Good Lungs'.

Statistical Method 2: Classification of Bad Vs. Good Lungs

Prediction Analysis of Microarray (PAM) is performed with DCD Start and End EVLP samples only.

Because of the findings in LIMMA, no DBD analysis was performed.

Prediction Analysis of Microarray (PAM)

PAM computes a standardized centroid for each class. This is the average intensity for each molecule in each class divided by the within-class standard deviation for that molecule.

Nearest centroid classification takes the intensity profile of a new sample, and compares it to each of these class centroids.

The class whose centroid that it is closest to, in squared distance, is the predicted class for that new sample.

To decide the shrinkage threshold, 10-fold cross-validation for a range of threshold values was performed.

The samples are divided up at random into 10 roughly equally sized parts. For each part in turn, the classifier is built on the other 9 parts then tested on the remaining part.

This is done for a range of threshold values, and the cross-validated misclassification error rate is reported for each threshold value.

The threshold value giving the minimum cross-validated misclassification error rate or a balance of error rate and no. of molecules used was chosen.

DCD Start EVLP

Out of 22 DCD lungs, there were 9 Bad Lungs and 13 Good Lungs.

The threshold value 1.06 is chosen and yields a subset of 68 selected metabolites with the lowest error rate 18% (FIG. 16C).

Analysis of DCD Samples at the Start of EVLP

List of 68 candidate metabolites (FIG. 16C).

The corresponding value from the LIMMA for each of the 68 metabolite is also given for comparison.

Candidate metabolites where the Adjusted p values are less than 0.05 are highlighted in bold.

DCD End EVLP

Out of 22 CDC lungs, there were 9 Bad Lungs and 13 Good Lungs.

The threshold value 1.99 is chosen and yields a subset of 16 selected molecules with the relative low error rate 18% (FIG. 17C).

Analysis of DCD Samples at the End of EVLP

List of 16 Candidate metabolites that Classify DCD lungs into Good or Bad categories (FIG. 17C).

Corresponding values from LIMMA also given.

Metabolites whose Adjusted p values are <0.05 are highlighted in bold.

For EVLP perfusates from DCD lungs at 1 hour EVLP, ten metabolites were able to distinguish Good Lungs from Bad lungs when an adjusted p value or False Discovery Rate (FDR)<0.10 was used as cut off. When using a more stringent cut off adjusted p value of <0.05 was employed, five metabolites were able to differentiate between Good and Bad Lungs (FIG. 14).

For EVLP perfusates from DCD lungs at 4 hour EVLP, forty metabolites were able to differentiate Good Lungs from Bad Lungs using an adjusted p value of <0.05 (FIG. 15).

However, for DBD lungs, whether at EVLP 1 hour or 4 hours, no metabolite was able to differentiate Good Lungs from Bad Lungs, regardless of a FDR of 0.05 or 0.1.

Classification of the sample using the metabolic profile of the perfusate was then performed, by employing PAM focusing on DCD lungs only, given the negative findings of DBD lungs.

Out of 22 DCD lungs, there were 9 Bad Lungs and 13 Good Lungs. For EVLP perfusate at 1 hour EVLP, the threshold value 1.06 is chosen (FIG. 16A, 16B). This yields a list of 68 candidate metabolites with the lowest error rate of 18% that could classify a given sample from 1 hour EVLP into Good vs. Bad Lung group (FIG. 16C).

Similarly, for EVLP perfusate at 4 hour EVLP, the threshold value 1.99 is chosen and yields a subset of 16 selected molecules with the relative low error rate 18% of classifying a given sample of 4 hour EVLP perfusate into Good vs. bad Lung group (FIG. 17A, 17B, 17C).

In compiling a preferred list of candidate EVLP perfusate metabolites that can serve as potential biomarkers that are capable of predicting whether a DCD donor lung is likely to have a good outcome (Good Lung) vs. a bad outcome (Bad Lung), the metabolites need to satisfy both criteria:

Capable of differentiating between 'Good Lungs' from 'Bad Lungs' using the ANOVA-type method LIMMA.

Capable of predicting whether a given lung belongs to 'Good Lung' or 'Bad Lung' category using the Classification method PAM.

List of Candidate Metabolites

In order to compile a preferred list of candidate metabolites that is statistically robust, the candidates need to satisfy the following criteria:

[1] metabolites that can differentiate between 'Good Lungs' from 'Bad Lungs' using the ANOVA-type method LIMMA.

[2] metabolites that can reliably predict whether a given lung belongs to 'Good Lung' or 'Bad Lung' category using the Classification method PAM.

The preferred list of candidate metabolites in DCD 1 hour EVLP perfusate and 4 hour EVLP perfusate are shown in FIGS. 18A and B.

Figure 19:
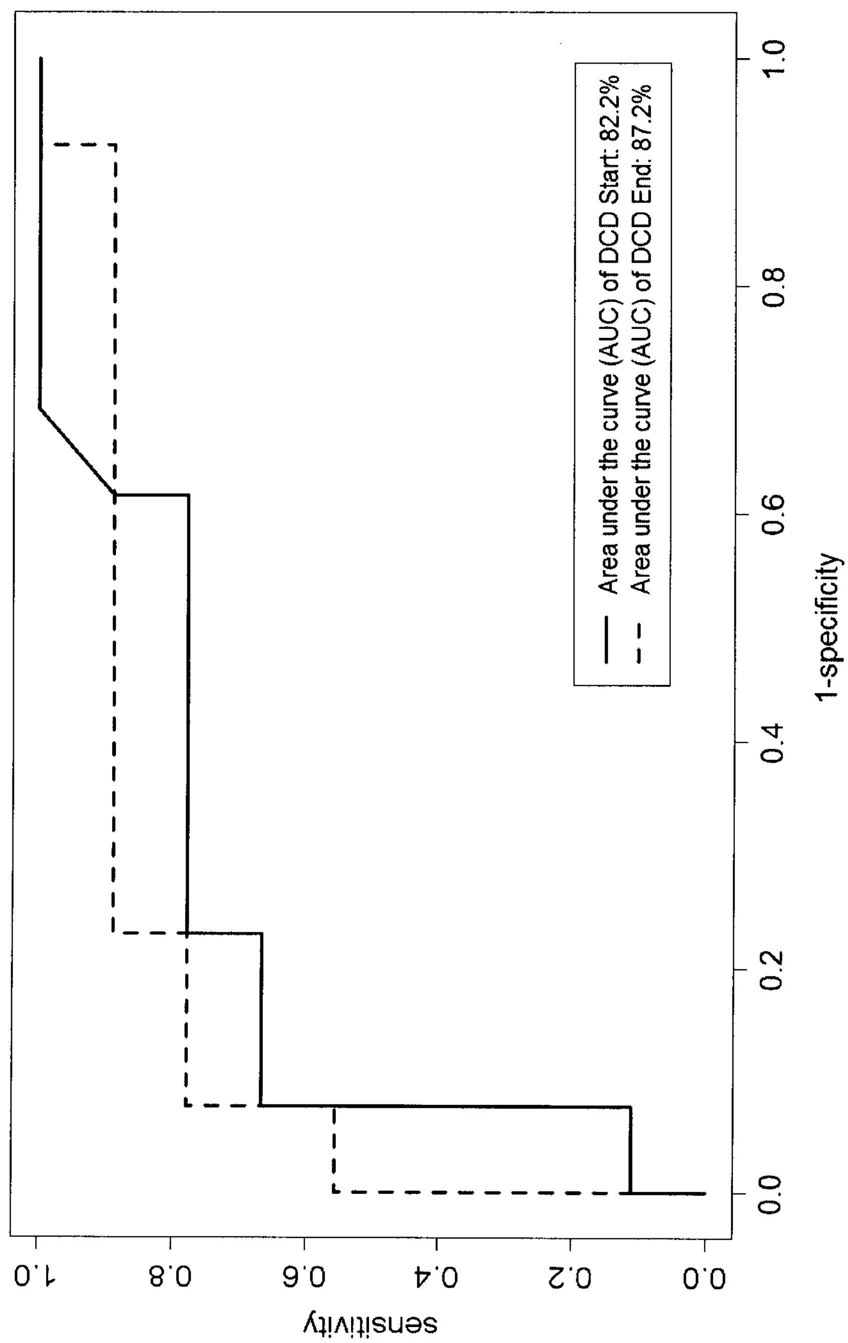
FIG. 19: Area Under the Curve plot for Candidate Metabolites in distinguishing between Good Lungs vs. Bad Lungs using DCD Lung EVLP test perfusate. Solid line for Start of EVLP and dashed line for End of EVLP.

Using this list of potential EVLP metabolic biomarkers, the Area Under the Curve in the Receiving Operator Characteristic plot achieves 82.2% for EVLP 1 hour in DCD lung perfusate, and 87.2% for EVLP 4 hour in DCD lung perfusate respectively (FIG. 19).

Conclusion

Using two independent and methodologically distinct statistical approaches, a number of metabolites to be potential biomarkers that appear capable of predicting the quality of DCD donor lungs assessed on EVLP were identified, with very encouraging AUC values in the 80% range.

These candidate biomarkers will be tested on a validation set of DCD EVLP perfusate samples in order to assess their sensitivity and specificity for biological validation.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Klein A S, Messersmith E E, Ratner L E, Kochik R, Baliga P K, Ojo A O. Organ donation and utilization in the United States, 1999-2008. American journal of transplantation. 2010; 10: 973-986.
2. de Perrot M, Liu M, Waddell T K, Keshavjee S. lschemia-reperfusion-induced lung injury. American Journal of Respiratory and Critical Care Medicine. 2003; 167:490-511.
3. Bharat A, Narayanan K, Street T, et al. Early posttransplant inflammation promotes the development of alloimmunity and chronic human lung allograft rejection. Transplantation. 2007; 83:150-158.
4. Whitson B A, Prekker M E, Herrington C S, et al. Primary graft dysfunction and long-term pulmonary function after lung transplantation. The Journal of heart and lung transplantation. 2007; 26:1004-1011.
5. Cypel M, Yeung J C, Liu M, Anraku M, Chen F, Karolak W, et al. Normothermic ex vivo lung perfusion in clinical lung transplantation. The New England journal of medicine. 2011; 364: 1431-1440.
6. Fischer S, Cassivi S D, Xavier a M, Cardella J a, Cutz E, Edwards V, et al. Cell death in human lung transplantation: apoptosis induction in human lungs during ischemia and after transplantation. Annals of surgery. 2000; 231: 424-431.
7. Pinsky D J, Liao H, Lawson C A, Yan S F, Chen J, Carmeliet P, et al. Coordinated induction of plasminogen activator inhibitor-1 (PAI-1) and inhibition of plasminogen activator gene expression by hypoxia promotes pulmonary vascular fibrin deposition. The Journal of clinical investigation. 1998; 102: 919-928.
8. Bombeli T, Karsan A, Tait J F, Harlan J M. Apoptotic vascular endothelial cells become procoagulant. Blood. 1997; 89: 2429-2442.
9. de Perrot M, Young K, Imai Y, Liu M, Waddell T K, Fischer S, et al. Recipient T cells mediate reperfusion injury after lung transplantation in the rat. Journal of immunology. 2003; 171: 4995-5002.
10. Quadri S M, Segall L, de Perrot M, Han B, Edwards V, Jones N, et al. Caspase inhibition improves ischemia-reperfusion injury after lung transplantation. American journal of transplantation. 2005; 5: 292-299.
11. Christie J D, Carby M, Bag R, Cords P, Hertz M, Weill D. Report of the ISHLT Working Group on Primary Lung Graft Dysfunction part II: definition. A consensus statement of the International Society for Heart and Lung Transplantation. The Journal of heart and lung transplantation. 2005; 24: 1454-1459.
12. Kramer G, Erdal H, Mertens HJMM, Nap M, Mauermann J, Steiner G, et al. Differentiation between cell death modes using measurements of different soluble forms of extracellular cytokeratin 18. Cancer research. 2004; 64:1751-1756.
13. Bell C W, Jiang W, Reich C F, Pisetsky D S. The extracellular release of HMGB1 during apoptotic cell death. American journal of physiology. Cell physiology. 2006; 291:01318-1325.
14. Urbonaviciute V, FUrnrohr B G, Meister S, Munoz L, Heyder P, De Marchis F, et al. Induction of inflammatory and immune responses by HMGB1-nucleosome complexes: implications for the pathogenesis of SLE. The Journal of experimental medicine. 2008; 205:3007-3018.
15. Abraham E, Arcaroli J, Carmody A, Wang H, Tracey K J. HMG-1 as a mediator of acute lung inflammation. Journal of immunology. 2000; 165:2950-2954.
16. Ueno H, Matsuda T, Hashimoto S, Amaya F, Kitamura Y, Tanaka M, et al. Contributions of high mobility group box protein in experimental and clinical acute lung injury. American journal of respiratory and critical care medicine. 2004; 170:1310-1316.
17. Wolfson R K, Chiang E T, Garcia J G N. HMGB1 induces human lung endothelial cell cytoskeletal rearrangement and barrier disruption. Microvascular research. 2011; 81:189-197.
18. Kawut S M, Okun J, Shimbo D, Lederer D J, De Andrade J, Lama V, et al. Soluble p-selectin and the risk of primary graft dysfunction after lung transplantation. Chest. 2009; 136:237-244.
19. Calfee C S, Budev M M, Matthay M A, Church G, Brady S, Uchida T, et al. Plasma receptor for advanced glycation end-products predicts duration of ICU stay and mechanical ventilation in patients after lung transplantation. The Journal of heart and lung transplantation. 2007; 26:675-80.
20. Christie J D, Shah C V, Kawut S M, Mangalmurti N, Lederer D J, Sonett J R, et al. Plasma levels of receptor for advanced glycation end products, blood transfusion, and risk of primary graft dysfunction. American journal of respiratory and critical care medicine. 2009; 15; 180: 1010-5.
21. Christie J D, Robinson N, Ware L B, Plotnick M, De Andrade J, Lama V, et al. Association of protein C and type 1 plasminogen activator inhibitor with primary graft dysfunction. American journal of respiratory and critical care medicine. 2007; 175:69-74.
22. Kaneda H, Waddell T K, de Perrot M, Bai X-H, Gutierrez C, Arenovich T, et al. Pre-implantation multiple cytokine mRNA expression analysis of donor lung grafts predicts survival after lung transplantation in humans. American journal of transplantation. 2006; 6:544-551.
23. Anraku M, Cameron M J, Waddell T K, Liu M, Arenovich T, Sato M, et al. Impact of human donor lung gene expression profiles on survival after lung transplantation: a case-control study. American journal of transplantation. 2008; 8:2140-2148.
24. Cypel M, Yeung J C, Liu M, Anraku M, Chen F, Karolak W, Sato M, Laratta J, Azad S, Madonik M, Chow C W, Chaparro C, Hutcheon M, Singer L G, Slutsky A S, Yasufuku K, de Perrot M, Pierre A F, Waddell T K, Keshavjee S. Normothermic ex vivo lung perfusion in clinical lung transplantation. N Engl J Med. 2011 Apr. 14; 364(15):1431-40.
25. Smyth G K. Linear Models and empirical bayes methods for assessing differential expression in microarray experiments. Stat Appl Genet Mol Biol. 2004; 3: Article3.
26. Benjamini Y, Hochberg Y. Controlling the False Discovery Rate: a practical and powerful approach to multiple testing. J R Statist Soc. 1995; 57(1):289-300.
27. Tibshirani R J, Efron B. Pre-validation and inference in microarrays. Stat Appl Genet Mol Biol. 2002; 1: Article1.

The invention claimed is:

1. A method of classifying a lung graft subjected to normothermic ex vivo lung perfusion (EVLP), during perfusion and/or after perfusion, the method comprising:

a) collecting a test sample from the lung graft, wherein the test sample is a donor lung tissue sample, a bronchoalveolar lavage sample and/or a perfusate sample optionally collected before, during or after transplant;

b) measuring a polypeptide level of each of one or more negative transplant predictor gene products selected from M-CSF, IL-8, SCGF-beta, GRO-alpha, G-CSF, MIP-1 alpha, MIP-1beta, endothelin 1 (ET-1), big ET-1, cytokeratin 18 (CK-18), caspase 3 and HMGB-1, in the test sample; and c) identifying the graft as a good candidate for transplant or a poor candidate for transplant wherein an increased polypeptide level of one or more negative transplant outcome predictor gene products compared to an outcome control is indicative the graft is a poor candidate for transplant.

2. The method of claim 1, wherein the graft is from a high risk donor after brain death (DBD) or a donor after cardiac death (DCD).

3. The method of claim 1, wherein the graft undergoes EVLP for at least 4 hours, optionally 4 to 6 hours.

4. The method of claim 1, wherein the test perfusate sample is collected during or after EVLP, optionally wherein the test perfusate sample is collected after 1 hour of EVLP, 2 hours of EVLP, 3 hours of EVLP or 4 hours of EVLP.

5. The method of claim 1, wherein the test perfusate sample is taken after about 30 minutes or after 1 hour of EVLP, and the negative transplant predictor gene products are selected from M-CSF, IL-8, SCGF-beta, ET-1 and big ET-1.

6. The method of claim 5, wherein:

a) the M-CSF polypeptide is measured and is increased at least 1.2×, 1.3×, 1.4×, 1.5×, 1.6×, 1.7×, 1.8×, 1.9× or 2× compared the outcome control;

b) the IL-8 polypeptide is measured and is increased at least 1.5×, 2×, 3×, 4×, 5×, 6×, 7×, 8×, 9× or 10× compared the outcome control;

c) the SCGF-beta polypeptide is measured and is increased at least 1.2×, 1.3×, 1.4×, 1.5×, 1.6×, 1.7×, 1.8×, 1.9× or 2× compared the outcome control;

d) ET-1 polypeptide is measured and is increased at least 1.2×, 1.3×, 1.4×, 1.5×, 1.6×, 1.7×, 1.8×, 1.9× or 2× compared to the outcome control; and/or e) the big ET-1 polypeptide is measured, and is increased at least 1.2×, 1.3×, 1.4×, 1.5×, 1.6×, 1.7×, 1.8×, 1.9× or 2× compared to the outcome control.

7. The method of claim 6, wherein the lung graft is identified as a poor candidate for transplant if after about 30 minutes or about 1 hour of EVLP:

a) the level of M-CSF polypeptide is greater than 30 pg/mL, 31 pg/mL, 32 pg/mL, 33 pg/mL, 34 pg/mL, 35 pg/mL, 36 pg/mL or 37 pg/mL, b) the level of IL-8 polypeptide is greater than 70 pg/mL, 72 pg/mL, 74 pg/mL, 76 pg/mL, 80 pg/mL, 82 pg/mL, 84 pg/mL or 86 pg/mL;

c) the level of SCGF-beta polypeptide is greater than 280 pg/mL, 290 pg/mL, 300 pg/mL, 310 pg/mL, 320 pg/mL, 330 pg/mL, 340 pg/mL or 350 pg/mL;

d) the level of ET-1 polypeptide is greater than 2 pg/mL, 2.2 pg/mL, 2.4 pg/mL, 2.6 pg/mL, 2.8 pg/mL, 3 pg/mL, 3.1 pg/mL or 3.2 pg/mL; and/or e) the level of big ET-1 polypeptide is greater than 8 pg/mL, 9 pg/mL, 10 pg/mL, 11 pg/mL, 12 pg/mL, 13 pg/mL, 14 pg/mL or 15 pg/mL.

8. The method of claim 1, wherein the test perfusate sample is taken after about 3 or 4 hours of EVLP and the negative transplant predictor gene products are selected from IL-8, GRO-alpha, G-CSF, MIP-1alpha, MIP-1beta ET-1, big ET-1, CK-18, caspase 3, and HMGB-1.

9. The method of claim 8, wherein:

a) the IL-8 polypeptide is measured and is increased at least 1.5×, 2×, 2.5×, 3×, 3.5× or 4×, compared the outcome control;

b) the GRO-alpha polypeptide is measured and is increased at least 1.5×, 2×, 2.5×, 3×, 3.5× or 4× compared the outcome control;

c) the G-CSF polypeptide is measured and is increased at least 1.2×, 1.3×, 1.4×, 1.5×, 1.6×, 1.7×, 1.8×, 1.9× or 2× compared to the outcome control;

d) the MIP-1alpha polypeptide is measured and is increased at least 1.5×, 2×, 2.5×, 3×, 3.5× or 4× compared to the outcome control;

e) the MIP-1beta polypeptide is measured and is increased at least 1.5×, 2×, 2.5×, 3×, 3.5× or 4× compared the outcome control;

f) the level of CK18 polypeptide is measured and is increased at least 1.2×, 1.3×, 1.4×, 1.5×, 1.6×, 1.7×, 1.8×, 1.9× or 2× compared to the outcome control; and/or g) the level of HMGB-1 polypeptide is measured and is increased at least 1.2×, 1.3×, 1.4×, 1.5×, 1.6×, 1.7×, 1.8×, 1.9× or 2× compared to the outcome control.

10. The method of claim 9, wherein the lung graft is identified as a poor candidate for transplant if after 4 hours of EVLP:

a) the level of IL-8 polypeptide is greater than 2000 pg/mL, 2250 pg/mL, 2500 pg/mL, 2750 pg/mL, 3000 pg/mL, 3250 pg/mL, 3500 pg/mL or 3750 pg/mL;

b) the level of GRO-alpha polypeptide is greater than 550 pg/mL, 600 pg/mL, 650 pg/mL, 700 pg/mL, 750 pg/mL, 800 pg/mL, 850 pg/mL or 900 pg/mL;

c) the level of G-CSF polypeptide is greater than 3500 pg/mL 4000 pg/mL, 4500 pg/mL, 5000 pg/mL, 5500 pg/mL, 6000 pg/mL, 6500 pg/mL or 7000 pg/mL;

d) the level of MIP-1alpha polypeptide is greater than 30 pg/mL, 35 pg/mL, 40 pg/mL, 45 pg/mL, 50 pg/mL, 55 pg/mL, 60 pg/mL 65 pg/mL, 70 pg/mL, 75 pg/mL, 80 pg/mL or 85 pg/mL;

e) level of MIP-1beta polypeptide is greater than 1000 pg/mL, 1500 pg/mL, 2000 pg/mL, 2500 pg/mL, 3000 pg/mL, 3500 pg/mL, 4000 pg/mL or 4500 pg/mL;

f) the level of ET-1 polypeptide is greater than 1.5 pg/mL, 1.7 pg/mL, 1.9 pg/mL, 2.1 pg/mL 2.3 pg/mL, 2.5 pg/mL, 2.7 pg/mL or 2.9 pg/mL;

g) the level of big ET-1 polypeptide is greater than 20 pg/mL, 22 pg/mL, 24 pg/mL, 26 pg/mL 28 pg/mL, 30 pg/mL, 32 pg/mL or 34 pg/mL;

h) the level of CK18 polypeptide is greater than 80 U/L, 84 U/L, 88 U/L, 92 U/L, 96 U/L or 100 U/L; and/or i) the level of HMGB-1 polypeptide is greater than 14 ng/mL, 15.6 ng/mL, 20 ng/mL, 25 ng/mL, 30 ng/mL, 35 ng/mL, 40 ng/mL, 50 ng/mL, 60 ng/mL, 70 ng/mL, 80 ng/mL or 90 ng/mL.

11. The method of claim 1, wherein the level of the one or more negative transplant predictor gene product is measured using ELISA, optionally wherein the levels of one or more of M-CSF, IL-8, SCGF-beta, GRO-alpha, G-CSF, MIP-1 alpha and/or MIP-1beta is assayed multiplex assays such as Bio-plex Pro™ Human cytokine 27-plex Assay and Bio-plex Pro™ Human Cytokine 21-plex Assay.

12. The method of claim 1, wherein the negative transplant predictor gene products are selected from ET-1, big ET-1, CK-18, caspase 3 and HMGB-1, and the polypeptide level is measured using an ET-1 detection antibody, a big ET-1 detection antibody, a HMGB-1 detection antibody, a M30 kit and/or a M65 kit.

13. The method of claim 1, wherein the test sample is a fluid sample.

* * * * *

UNITED STATES PATENT AND TRADEMARK OFFICE

CERTIFICATE OF CORRECTION

PATENT NO. : 9,835,630 B2
APPLICATION NO. : 14/768948
DATED : December 5, 2017
INVENTOR(S) : Shaf Keshavjee, Marcelo Cyper and Mingyao Liu It is certified that error appears in the above-identified patent and that said Letters Patent is hereby corrected as shown below:

Claim 1, Column 37, Line 5 should read:
from: M-CSF, IL-8, SCGF-beta, GRO-alpha, G-CSF, Claim 6, Column 37, Line 38 should read:
d) the ET-1 polypeptide is measured and is increased at least Claim 10, Column 38, Line 34 should read:
pg/mL, 60 pg/mL, 65 pg/mL, 70 pg/mL, 75 pg/mL, 80

Claim 10, Column 38, Line 40 should read:
1.7 pg/mL, 1.9 pg/mL, 2.1 pg/mL, 2.3 pg/mL, 2.5

Claim 10, Column 38, Line 43 should read:
pg/mL, 22 pg/mL, 24 pg/mL, 26 pg/mL, 28 pg/mL, 30

Claim 11, Column 38, Line 53 should read:
MIP-1 alpha and/or MIP-beta is assayed using a multiplex assay Signed and Sealed this
Thirteenth Day of March, 2018

Andrei Iancu
*Director of the United States Patent and Trademark Office*